(12) United States Patent
Tatsuta

(10) Patent No.: US 7,595,415 B2
(45) Date of Patent: Sep. 29, 2009

(54) α-SUBSTITUTED VINYLTIN COMPOUND

(75) Inventor: Kuniaki Tatsuta, Suginami-ku (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 11/911,589

(22) PCT Filed: Apr. 14, 2006

(86) PCT No.: PCT/JP2006/307972

§ 371 (c)(1),
(2), (4) Date: Oct. 15, 2007

(87) PCT Pub. No.: WO2006/112413

PCT Pub. Date: Oct. 26, 2006

(65) Prior Publication Data

US 2009/0023939 A1    Jan. 22, 2009

(30) Foreign Application Priority Data

Apr. 14, 2005 (JP) ............................. 2005-117593
Dec. 20, 2005 (JP) ............................. 2005-365795

(51) Int. Cl.
*C07F 7/00* (2006.01)
(52) U.S. Cl. ..................... 556/95; 556/87; 556/105; 556/107
(58) Field of Classification Search ............... 556/87, 556/95, 105, 107
See application file for complete search history.

(56) References Cited

U.S. PATENT DOCUMENTS

2005/0107619 A1    5/2005    Grammenos et al.
2005/0181948 A1    8/2005    Grammenos et al.
2005/0282730 A1    12/2005    Miyaji et al.

FOREIGN PATENT DOCUMENTS

| JP | 2-40324 | 2/1990 |
|---|---|---|
| JP | 2-304058 | 12/1990 |
| JP | 4-182427 | 6/1992 |
| JP | 7-69883 | 3/1995 |
| JP | 2004-115504 | 4/2004 |
| WO | 03/076392 | 9/2003 |
| WO | 03/082822 | 10/2003 |
| WO | 2004/016264 | 2/2004 |

OTHER PUBLICATIONS

Tatsuta, Kuniaki et al., "The First Stereoselective Total Synthesis of Antiviral Antibiotic, Xanthocillin X Dimethylether and its Stereoisomer", Tetrahedron Letters, vol. 46, No. 30, pp. 5017 to 5020, 2005.

Mitchell, Terence N. et al., "Addition of Stannyl Phosphines to Alkynes and Allenes", Journal of Organometallic Chemistry, vol. 386, No. 2, pp. 167 to 176, 1990.

*Primary Examiner*—Porfirio Nazario Gonzalez
(74) *Attorney, Agent, or Firm*—Oblon, Spivak, McClelland, Maier & Neustadt, L.L.P.

(57) ABSTRACT

To provide α-substituted vinyltin useful for the search for function-developing substances such as pharmaceuticals/agrichemicals and functional materials and for the construction of a compound library.

An α-substituted vinyltin compound represented by the formula (1), a tautomer or salt of the compound or a solvate thereof:

$$R^2CH{=}C(R^3)Sn(R^1)_3 \qquad (1)$$

wherein $R^1$ is a $C_{1-10}$ alkyl group, a $C_{2-14}$ aryl group or the like, $R^2$ is a $C_{2-14}$ aryl group, a $C_{2-9}$ heterocyclyl group, a $C_{3-10}$ cycloalkyl group or the like, and $R^3$ is a carbamoyl group, a thiocarbamoyl group, an isocyanate group, an isothiocyanate group, a formylamino group, a thioformylamino group, an isonitrile group, an urea group, a carbamate group or the like.

24 Claims, No Drawings

α-SUBSTITUTED VINYLTIN COMPOUND

TECHNICAL FIELD

The present invention relates to α-substituted vinyltin compounds.

A vinyltin compound is a useful intermediate capable of introducing a wide range of substituents by means of coupling reaction to tin. In addition, an α-substituted vinyltin compound further having a functional group having reactivity different from that of a tin functional group at the α-position is a useful compound capable of preparing an α,α-disubstituted vinyl compound by further introduction of a substituent or conversion of a functional group.

BACKGROUND ART

A compound having a tin functional group has been known to be converted to various compounds e.g. by Stille reaction (e.g. Non-Patent Documents 1, 2, 3 and 4). Further, it has been known to undergo homocoupling in the presence of a palladium catalyst (e.g. Non-Patent Document 5).

Further, it has been known that in a compound having a vinyltin functional group, the tin functional group is further stereoselectively converted to a halide atom as the case requires (e.g. Non-Patent Documents 6, 7, 8, 20, 21 and 22) and that a vinyl halide compound reacts with various organometric reagents (e.g. Non-Patent Documents 4, 20, 21 and 22).

On the other hand, a compound having a carbamoyl group or a thiocarbamoyl group may undergo, for example, Curtius rearrangement using lead tetraacetate to prepare a compound having an isocyanate group or a isothiocyanate group (e.g. Non-Patent Document 9).

An isocyanate group and an isothiocyanate group can be converted to various substituents utilizing their reactivity. For example, they are useful for preparation of a urea compound or a thiourea compound by reaction with an amine (e.g. Non-Patent Document 10) or of a carbamate compound or a thiocarbamate compound by reaction with an alcohol (e.g. Non-Patent Document 11).

Further, in preparation of an isocyanate compound or a thioisocyanate compound, by subsequent reaction with an amine or an alcohol directly without isolation and purification, a urea compound or a carbamate compound can be prepared (e.g. Non-Patent Document 12).

Further, by reducing a compound having an isocyanate group or an isothiocyanate group, a compound having a formylamino group or a thioformylamino group can be obtained (e.g. Non-Patent Document 13). Such groups can be converted to an isonitrile group by the action of p-tosyl chloride (e.g. Non-Patent Document 14) or phosphorus oxychloride (e.g. Non-Patent Document 15).

Many compounds having an isonitrile group are present naturally and develop various physiological activities (e.g. Non-Patent Document 16). As one example, xanthocillin X analogs may be mentioned. Xanthocillin analogs have been known to have a wide range of antimicrobial action and have been reported to have antiviral action, VEGF and COX-2 inhibitory action (e.g. Patent Document 1), aromatase inhibitory action (e.g. Patent Document 2), antitumor action (e.g. Patent Documents 3 and 4), insecticidal action (e.g. Patent Document 5), etc. in addition. Further, as found by the applicants, they are useful compounds which have been known to have thrombopoietin receptor affinity and agonist activity (e.g. Patent Document 6).

Further, by utilizing an isonitrile group which is a reactive functional group, a group of compounds can be prepared by utilizing Ugi reaction and Passerini reaction (e.g. Non-Patent Documents 17, 18 and 19).

As α-substituted vinyltin compounds having a reactive functional group at the α-position in addition to a tin functional group, the following have been known, but one having a nitrogen functional group or one having a carbamoyl group as its starting material has not yet been known.

1) α-alkylcarbonyl-vinyltin compounds and α-arylcarbonyl-vinyltin compounds (e.g. Non-Patent Document 20).

2) α-silyl-substituted vinyltin compounds and α-alkoxycarbonyl-substituted vinyltin compounds (e.g. Non-Patent Documents 21 and 22).

3) α-alkylaminocarbonyl-substituted vinyltin compounds which are vinyltin compounds having a nitrogen functional group at the α-position, for which patents have been applied by BASF (e.g. Patent Documents 7 and 8).

Non-Patent Document 1: Journal of the American Chemistry Society, 100, p. 3636 (1978).
Non-Patent Document 2: Journal of the American Chemistry Society, 101, p. 4992 (1979).
Non-Patent Document 3: Angewandte Chemie International Edition in English, 25, p. 508 (1997).
Non-Patent Document 4: Organic Reaction, 50, p. 1-652 (1997).
Non-Patent Document 5: Tetrahedron Letters, 42, p. 7729 (2001).
Non-Patent Document 6: Journal of Medicinal Chemistry, Vol. 45, No. 6, p. 1253 (2002).
Non-Patent Document 7: Journal of Medicinal Chemistry, Vol. 46, No. 6, p. 925 (2003).
Non-Patent Document 8: Organic Letters, Vol. 4, No. 20, p. 3391 (2002).
Non-Patent Document 9: Journal of Organic Chemistry, 40, p. 3554 (1975).
Non-Patent Document 10: Chemische Berichte, 81, p. 36 (1948).
Non-Patent Document 11: Synthesis, p. 131 (1989).
Non-Patent Document 12: Journal of Organic Chemistry, 24, p. 3554 (1975).
Non-Patent Document 13: Journal of the American Chemistry Society, 95, p. 1669 (1973).
Non-Patent Document 14: Journal of Organic Chemistry, 23, p. 1221 (1958).
Non-Patent Document 15: Bioscience, Biotechnology, and Biochemistry, 57(4), p. 659 (1993).
Non-Patent Document 16: Angewandte Chemie International Edition in English, 39, p. 3168 (2000).
Non-Patent Document 17: Angewandte Chemie International Edition in English, 39, p. 3168 (2000).
Non-Patent Document 18: Organic Letters, 6, p. 4231 (2004).
Non-Patent Document 19: Molecules, 8, p. 53 (2003). http://www.mdpi.org/
Non-Patent Document 20: TETRAHEDRON, Vol. 49, No. 21, p. 4677 (1993).
Non-Patent Document 21: TETRAHEDRON, Vol. 48, No. 40, p. 8801 (1992).
Non-Patent Document 22: Tetrahedron Letters, Vol. 33, No. 31, p. 4495 (1992).
    Patent Document 1: JP-A-2004-115504
    Patent Document 2: JP-A-7-69883
    Patent Document 3: JP-A-2-304058
    Patent Document 4: JP-A-4-182427
    Patent Document 5: JP-A-2-40324
    Patent Document 6: WO2004/016264

Patent Document 7: WO03/076392
Patent Document 8: WO03/082822

DISCLOSURE OF THE INVENTION

Object to be Accomplished by the Invention

α-substituted vinyltin compounds having a tin functional group and at the α-position, a carbamoyl group, a thiocarbamoyl group, an isocyanate group, an isothiocyanate group, a formylamino group, a thioformylamino group, an isonitrile group, an urea group, a carbamate group or the like, have functional groups differing in the reactivity and are thereby capable of being converted to various compounds sequentially by introduction of a substituent or conversion of a functional group depending on the reactivity and are very useful. Further, various analogs can be prepared from a common intermediate, and the present invention is particularly useful for the search for function-developing substances such as pharmaceuticals/agrichemicals and functional materials and for the construction of a compound library.

Means to Accomplish the Object

The present inventor has conducted extensive studies to find such useful α-substituted vinyltin compounds and as a result, found compounds of the present invention and accomplished the present invention.

Namely, the present invention provides the following.
1. An α-substituted vinyltin compound represented by the formula (1), a tautomer or salt of the compound or a solvate thereof:

$$R^2CH=C(R^3)Sn(R^1)_3 \quad (1)$$

wherein $R^1$ is a $C_{1-10}$ alkyl group (the $C_{1-10}$ alkyl group may be substituted by a halogen atom) or a $C_{2-14}$ aryl group (the $C_{2-14}$ group may be substituted by a $C_{1-6}$ alkyl group (the $C_{1-6}$ alkyl group may be substituted by a halogen atom) or a halogen atom);
$R^2$ is a $C_{2-14}$ aryl group, a $C_{2-9}$ heterocyclyl group or a $C_{3-10}$ cycloalkyl group (each of the $C_{2-14}$ aryl group, $C_{2-9}$ heterocyclyl group and $C_{3-10}$ cycloalkyl group may optionally be substituted by a substituent represented by —W$^1$(CW$^2$W$^3$)mW$^4$ (wherein W$^1$ is (CR$^5$R$^6$)n (wherein R$^5$ and R$^6$ are each independently a hydrogen atom or a $C_{1-6}$ alkyl group (the $C_{1-6}$ alkyl group may be substituted by a halogen atom) or they together form O= or S=, and n is 0, 1, 2 or 3), an oxygen atom, a sulfur atom or NR$^7$ (wherein R$^7$ is a hydrogen atom, a $C_{1-6}$ alkyl group, a formyl group or a $C_{1-6}$ alkylcarbonyl group), W$^2$ and W$^3$ are each independently a hydrogen atom or a $C_{1-3}$ alkyl group (the $C_{1-3}$ alkyl group may be substituted by a halogen atom), m is 0, 1, 2 or 3, and W$^4$ is a hydrogen atom, a hydroxyl group, a protected hydroxyl group, a thiol group, a protected thiol group, an amino group, a protected amino group, a formyl group, a halogen atom, a nitro group, a cyano group, a $C_{1-10}$ alkyl group, a $C_{1-10}$ thioalkyl group, a $C_{2-10}$ alkenyl group, a $C_{2-6}$ alkynyl group, a $C_{2-9}$ heterocyclyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (each of the $C_{1-10}$ alkyl group, $C_{1-10}$ thioalkyl group, $C_{2-10}$ alkenyl group, $C_{2-6}$ alkynyl group, $C_{2-9}$ heterocyclyl group, $C_{1-10}$ alkoxy group, $C_{1-10}$ alkylcarbonyloxy group, $C_{1-10}$ alkylcarbonylamino group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a thiol group, a protected thiol group, a phosphonic acid group, a phosphonic acid $C_{1-6}$ alkyl ester group, a protected phosphonic acid group, a sulfonic acid group, a sulfonic acid $C_{1-6}$ alkyl ester group, a protected sulfonic acid group, a tetrazole group, a protected tetrazole group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), S(=O)$_2$R$^8$, P(=O)$_2$R$^8$, S(=O)R$^8$, C(=O)R$^8$, C(=S)R$^8$ (wherein R$^8$ is a hydroxyl group, a protected hydroxyl group, a $C_{1-10}$ alkyl group, a $C_{2-10}$ alkenyl group, a $C_{2-6}$ alkynyl group, a $C_{2-9}$ heterocyclyl group, a $C_{1-10}$ alkoxy group (each of the $C_{1-10}$ alkyl group, $C_{2-10}$ alkenyl group, $C_{2-6}$ alkynyl group, $C_{2-9}$ heterocyclyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group, a $C_{2-14}$ aryloxy group (each of the $C_{2-14}$ aryl group and $C_{2-14}$ aryloxy group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or NR$^9$R$^{10}$ (wherein R$^9$ and R$^{10}$ are each independently a hydrogen atom, a hydroxyl group, a protected hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a is halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^9$ and $R^{10}$ together form —$(CH_2)_{m1}$-G-$(CH_2)_{m2}$— (wherein G is an oxygen atom, a sulfur atom, $CR^{11}R^{12}$ (wherein $R^{11}$ and $R^{12}$ are each independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{13}$ (wherein $R^{13}$ is a hydrogen atom, a hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m1 and m2 are each independently an integer of from 0 to 5, provided that m1+m2 is 3, 4 or 5))), a tetrazole group or a protected tetrazole group)); and $R^3$ is a carbamoyl group, a thiocarbamoyl group, an isonitrile group, an isocyanate group, an isothiocyanate group, a formylamino group, a thioformylamino group, or —NH(C=X)$R^4$ (wherein X is an oxygen atom or a sulfur atom, $R^4$ is a $C_{1-10}$ thioalkyl group, a $C_{1-10}$ alkoxy group (each of the $C_{1-10}$ thioalkyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^{14}R^{15}$ (wherein $R^{14}$ and $R^{15}$ are each independently a hydrogen atom, a hydroxyl group, a protected hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m3 and m4 are each independently an integer of from 0 to 5, provided that m3+m4 is 3, 4 or 5))).

2. The α-substituted vinyltin compound, a tautomer or salt of the compound or a solvate thereof according to the above 1, which is an E-isomer or a Z-isomer.

3. The α-substituted vinyltin compound, a tautomer or salt of the compound or a solvate thereof according to the above 2, wherein $R^2$ is a $C_{2-14}$ aryl group (the $C_{2-14}$ aryl group may optionally be substituted by a substituent represented by —$W^1(CW^2W^3)mW^4$ (wherein $W^1$ is $(CR^5R^6)n$ (wherein $R^5$ and $R^6$ are each independently a hydrogen atom or a $C_{1-6}$ alkyl group (the $C_{1-6}$ alkyl group may be substituted by a halogen atom) or they together form O= or S=, and n is 0, 1, 2 or 3), an oxygen atom, a sulfur atom or $NR^7$ (wherein $R^7$ is a hydrogen atom, a $C_{1-6}$ alkyl group, a formyl group or a $C_{1-6}$ alkylcarbonyl group), $W^2$ and $W^3$ are each independently a hydrogen atom or a $C_{1-3}$ alkyl group (the $C_{1-3}$ alkyl group may be substituted by a halogen atom), m is 0, 1, 2 or 3, and $W^4$ is a hydrogen atom, a hydroxyl group, a protected hydroxyl group, a thiol group, a protected thiol group, an amino group, a protected amino group, a formyl group, a halogen atom, a nitro group, a cyano group, a $C_{1-10}$ alkyl group, a $C_{1-10}$ thioalkyl group, a $C_{2-6}$ alkenyl group, a $C_{2-6}$ alkynyl group, a $C_{2-9}$ heterocyclyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (each of the $C_{1-10}$ alkyl group, $C_{1-10}$ thioalkyl group, $C_{2-6}$ alkenyl group, $C_{2-6}$ alkynyl group, $C_{2-9}$ heterocyclyl group, $C_{1-10}$ alkoxy group, $C_{1-10}$ alkylcarbonyloxy group, $C_{1-10}$ alkylcarbonylamino group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a thiol group, a protected thiol group, a phosphonic acid group, a phosphonic acid $C_{1-6}$ alkyl ester group, a protected phosphonic acid group, a sulfonic acid group, a sulfonic acid $C_{1-6}$ alkyl ester group, a protected sulfonic acid group, a tetrazole group, a protected tetrazole group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), $S(=O)_2R^8$, $S(=O)R^8$, $P(=O)_2R^8$, $C(=O)R^8$, $C(=S)R^8$ (wherein $R^8$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclyl group, a $C_{1-10}$ alkoxy group (each of the $C_{1-10}$ alkyl group, $C_{2-6}$ alkenyl group, $C_{2-6}$ alkynyl group, $C_{2-9}$ heterocyclyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group, a $C_{2-14}$ aryloxy group (each of the $C_{2-14}$ aryl group and $C_{2-14}$ aryloxy group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^9R^{10}$ (wherein $R^9$ and $R^{10}$ are each independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^9$ and $R^{10}$ together form —$(CH_2)_{m1}$-G-$(CH_2)_{m2}$— (wherein G is an oxygen atom, a sulfur atom, CR$^{11}$R$^{12}$ (wherein R$^{11}$ and R$^{12}$ are each independently a hydrogen atom, a C$_{1-10}$ alkyl group, a C$_{2-14}$ aryl group, a C$_{1-10}$ alkoxy group, a C$_{2-14}$ aryloxy group, a hydroxyl group or a protected hydroxyl group) or NR$^{13}$ (wherein R$^{13}$ is a hydrogen atom, a hydroxyl group, a formyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyloxy group, a C$_{1-10}$ alkoxycarbonyl group, a C$_{1-10}$ alkylsulfonyl group, a C$_{1-10}$ alkylcarbonyl group (each of the C$_{1-10}$ alkyl group, C$_{2-6}$ alkenyl group, C$_{2-6}$ alkynyl group, C$_{1-10}$ alkoxy group, C$_{1-10}$ alkylcarbonyloxy group, C$_{1-10}$ alkoxycarbonyl group, C$_{1-10}$ alkylsulfonyl group and C$_{1-10}$ alkylcarbonyl group may optionally be substituted by a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a protected amino group, a mono- or di-C$_{1-10}$ alkylamino group, a hydroxyl group, a protected hydroxyl group, a C$_{2-14}$ aryl group or a C$_{2-14}$ aryloxy group (each of the C$_{2-14}$ aryl group and C$_{2-14}$ aryloxy group may be substituted by a C$_{1-6}$ alkyl group (the C$_{1-6}$ alkyl group may be substituted by a halogen atom) or a halogen atom)) or a C$_{2-14}$ aryl group (the C$_{2-14}$ aryl group may optionally be substituted by a C$_{1-10}$ alkyl group (the C$_{1-10}$ alkyl group may be substituted by a halogen atom), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a protected amino group, a mono- or di-C$_{1-10}$ alkylamino group, a hydroxyl group, a protected hydroxyl group, a C$_{2-14}$ aryl group or a C$_{2-14}$ aryloxy group (each of the C$_{2-14}$ aryl group and C$_{2-14}$ aryloxy group may be substituted by a C$_{1-6}$ alkyl group (the C$_{1-6}$ alkyl group may be substituted by a halogen atom) or a halogen atom))), and m1 and m2 are each independently an integer of from 0 to 5, provided that m1+m2 is 3, 4 or 5))), a tetrazole group or a protected tetrazole group)).

4. The α-substituted vinyltin compound, a tautomer or salt of the compound or a solvate thereof according to the above 2, wherein R$^2$ is a phenyl group (the phenyl group may optionally be substituted by a substituent represented by —W$^1$(CW$^2$W$^3$)mW$^4$ (wherein W$^1$ is (CR$^5$R$^6$)n (wherein R$^5$ and R$^6$ are each independently a hydrogen atom or a C$_{1-6}$ alkyl group (the C$_{1-6}$ alkyl group may be substituted by a halogen atom) or they together form O= or S=, and n is 0, 1, 2 or 3), an oxygen atom, a sulfur atom or NR$^7$ (wherein R$^7$ is a hydrogen atom, a C$_{1-6}$ alkyl group, a formyl group or a C$_{1-6}$ alkylcarbonyl group), W$^2$ and W$^3$ are each independently a hydrogen atom or a C$_{1-3}$ alkyl group (the C$_{1-3}$ alkyl group may be substituted by a halogen atom), m is 0, 1, 2 or 3, and W$^4$ is a hydrogen atom, a hydroxyl group, a protected hydroxyl group, a thiol group, a protected thiol group, an amino group, a protected amino group, a formyl group, a halogen atom, a nitro group, a cyano group, a C$_{1-10}$ alkyl group, a C$_{1-10}$ thioalkyl group, a C$_{2-6}$ alkenyl group, a C$_{2-6}$ alkynyl group, a C$_{2-9}$ heterocyclyl group, a C$_{1-10}$ alkoxy group, a C$_{1-10}$ alkylcarbonyloxy group, a C$_{1-10}$ alkylcarbonylamino group, a mono- or di-C$_{1-10}$ alkylamino group (each of the C$_{1-10}$ alkyl group, C$_{1-10}$ thioalkyl group, C$_{2-6}$ alkenyl group, C$_{2-6}$ alkynyl group, C$_{2-9}$ heterocyclyl group, C$_{1-10}$ alkoxy group, C$_{1-10}$ alkylcarbonyloxy group, C$_{1-10}$ alkylcarbonylamino group and mono- or di-C$_{1-10}$ alkylamino group may optionally be substituted by a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a protected amino group, a mono- or di-C$_{1-10}$ alkylamino group, a hydroxyl group, a protected hydroxyl group, a phenyl group or a phenyloxy group (each of the phenyl group and phenyloxy group may be substituted by a C$_{1-6}$ alkyl group (the C$_{1-6}$ alkyl group may be substituted by a halogen atom) or a halogen atom)), a phenyl group (the phenyl group may optionally be substituted by a C$_{1-10}$ alkyl group (the C$_{1-10}$ alkyl group may be substituted by a halogen atom), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a protected amino group, a mono- or di-C$_{1-10}$ alkylamino group, a hydroxyl group, a protected hydroxyl group, a thiol group, a protected thiol group, a phosphonic acid group, a phosphonic acid C$_{1-6}$ alkyl ester group, a protected phosphonic acid group, a sulfonic acid group, a sulfonic acid C$_{1-6}$ alkyl ester group, a protected sulfonic acid group, a tetrazole group, a protected tetrazole group, a phenyl group or a phenyloxy group (each of the phenyl group and phenyloxy group may be substituted by a C$_{1-6}$ alkyl group (the C$_{1-6}$ alkyl group may be substituted by a halogen atom) or a halogen atom)), S(=O)$_2$R$^8$, S(=O)R$^8$, P(=O)$_2$R$^8$, C(=O)R$^8$, C(=S)R$^8$ (wherein R$^8$ is a hydroxyl group, a protected hydroxyl group, a C$_{1-10}$ alkyl group, a C$_{2-6}$ alkenyl group, a C$_{2-6}$ alkynyl group, a C$_{2-9}$ heterocyclyl group, a C$_{1-10}$ alkoxy group (each of the C$_{1-10}$ alkyl group, C$_{2-6}$ alkenyl group, C$_{2-6}$ alkynyl group, C$_{2-9}$ heterocyclyl group and C$_{1-10}$ alkoxy group may optionally be substituted by a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a protected amino group, a mono- or di-C$_{1-10}$ alkylamino group, a hydroxyl group, a protected hydroxyl group, a phenyl group or a phenyloxy group (each of the phenyl group and phenyloxy group may be substituted by a C$_{1-6}$ alkyl group (the C$_{1-6}$ alkyl group may be substituted by a halogen atom) or a halogen atom)), a phenyl group, a phenyloxy group (each of the phenyl group and phenyloxy group may optionally be substituted by a C$_{1-10}$ alkyl group (the C$_{1-10}$ alkyl group may be substituted by a halogen atom), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a protected amino group, a mono- or di-C$_{1-10}$ alkylamino group, a hydroxyl group, a protected hydroxyl group, a phenyl group or a phenyloxy group (each of the phenyl group and phenyloxy group may be substituted by a C$_{1-6}$ alkyl group (the C$_{1-6}$ alkyl group may be substituted by a halogen atom) or a halogen atom)) or NR$^9$R$^{10}$ (wherein R$^9$ and R$^{10}$ are each independently a hydrogen atom, a hydroxyl group, a protected hydroxyl group, a formyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyloxy group, a C$_{1-10}$ alkoxycarbonyl group, a C$_{1-10}$ alkylsulfonyl group, a C$_{1-10}$ alkylcarbonyl group (each of the C$_{1-10}$ alkyl group, C$_{2-6}$ alkenyl group, C$_{2-6}$ alkynyl group, C$_{1-10}$ alkoxy group, C$_{1-10}$ alkylcarbonyloxy group, C$_{1-10}$ alkoxycarbonyl group, C$_{1-10}$ alkylsulfonyl group and C$_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)) or a phenyl group (the phenyl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)), or $R^9$ and $R^{10}$ together form —$(CH_2)_{m1}$-G-$(CH_2)_{m2}$— (wherein G is an oxygen atom, a sulfur atom, $CR^{11}R^{12}$ (wherein $R^{11}$ and $R^{12}$ are each independently a hydrogen atom, a $C_{1-10}$ alkyl group, a phenyl group, a $C_{1-10}$ alkoxy group, a phenyloxy group, a hydroxyl group or a protected hydroxyl group) or $NR^{13}$ (wherein $R^{13}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)) or a phenyl group (the phenyl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom))), and m1 and m2 are each independently an integer of from 0 to 5, provided that m1+m2 is 3, 4 or 5))), a tetrazole group or a protected tetrazole group)).

5. The α-substituted vinyltin compound, a tautomer or salt of the compound or a solvate thereof according to any one of the above 2 to 4, wherein $R^3$ is a carbamoyl group or a thiocarbamoyl group.

6. The α-substituted vinyltin compound, a tautomer or salt of the compound or a solvate thereof according to any one of the above 2 to 4, wherein $R^3$ is a formylamino group or a thioformylamino group.

7. The α-substituted vinyltin compound, a tautomer or salt of the compound or a solvate thereof according to any one of the above 2 to 4, wherein $R^3$ is an isonitrile group.

8. The α-substituted vinyltin compound, a tautomer or salt of the compound or a solvate thereof according to any one of the above 2 to 4, wherein $R^3$ is an isocyanate group or an isothiocyanate group.

9. The α-substituted vinyltin compound, a tautomer or salt of the compound or a solvate thereof according to any one of the above 2 to 4, wherein $R^3$ is —NH(C=X)$R^4$ (wherein X is an oxygen atom or a sulfur atom, $R^4$ is a $C_{1-10}$ thioalkyl group, a $C_{1-10}$ alkoxy group (each of the $C_{1-10}$ thioalkyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^{14}R^{15}$ (wherein $R^{14}$ and $R^{15}$ are each independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^{14}$ and $R^{15}$ together form —$(CH_2)_{m3}$-J-$(CH_2)_{m4}$— (wherein J is an oxygen atom, a sulfur atom, $CR^{16}R^{17}$ (wherein $R^{16}$ and $R^{17}$ are each independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{18}$ (wherein $R^{18}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m3 and m4 are each independently an integer of from 0 to 5, provided that m3+m4 is 3, 4 or 5))).

10. The α-substituted vinyltin compound, a tautomer or salt of the compound or a solvate thereof according to any one of the above 2 to 4, wherein $R^3$ is —NH(C=X)$R^4$ (wherein X is an oxygen atom or a sulfur atom, and $R^4$ is a $C_{1-10}$ thioalkyl group, a $C_{1-10}$ alkoxy group or a mono- or di-$C_{1-10}$ alkylamino group (each of the $C_{1-10}$ thioalkyl group, $C_{1-10}$ alkoxy group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))).

11. The α-substituted vinyltin compound, a tautomer or is salt of the compound or a solvate thereof according to any one of the above 1 to 10, wherein $R^1$ is a $C_{1-6}$ alkyl group.

12. The α-substituted vinyltin compound, a tautomer or salt of the compound or a solvate thereof according to any one of the above 1 to 10, wherein $R^1$ is a phenyl group.

BEST MODE FOR CARRYING OUT THE INVENTION

Now, the present invention will be described in detail.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Naphthyl" denotes naphthyl, "Me" denotes methyl, "Et" denotes ethyl, "Pr" denotes propyl, "Bu" denotes butyl, "Ms" donates methanesulfonyl, "Tf" donates trifluoromethanesulfonyl and "Ts" denotes p-toluenesulfonyl.

First, the terms in the respective substituents $R^1$ to $R^{18}$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl or the like may be mentioned.

A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl or the like may be mentioned.

A $C_{1-10}$ alkyl group may be linear, branched or a $C_{3-10}$ cycloalkyl group, and in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl, c-heptyl, c-octyl, 1-methyl-c-hexyl, 2-methyl-c-hexyl, 3-methyl-c-hexyl, 1,2-dimethyl-c-hexyl, 1-ethyl-c-hexyl, 1-methyl-c-pentyl, 2-methyl-c-pentyl, 3-methyl-c-pentyl or the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 2-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl or the like may be mentioned.

A $C_{2-10}$ alkynyl group may be linear, branched or a $C_{3-10}$ cycloalkynyl group, and in addition to those mentioned above, 1-methyl-n-hexynyl, 1,2-dimethyl-n-hexynyl, 1-ethyl-n-hexynyl, 1-n-heptynyl, 2-n-heptynyl, 3-n-heptynyl, 4-n-heptynyl, 1-n-octynyl, 2-n-octynyl, 3-n-octynyl or the like may be mentioned.

A $C_{2-6}$ alkenyl group may be linear, branched or a $C_{3-6}$ cycloalkenyl group, and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl or the like may be mentioned.

A $C_{2-10}$ alkenyl group may be linear, branched or a $C_{3-10}$ cycloalkenyl group, and in addition to those mentioned above, 1-methyl-n-hexenyl, 1,2-dimethyl-n-hexenyl, 1-ethyl-n-hexenyl, 1-n-heptenyl, 2-n-heptenyl, 3-n-heptenyl, 4-n-heptenyl, 1-n-octenyl, 2-n-octenyl, 3-n-octenyl, 1-methyl-c-hexenyl, 1,2-dimethyl-c-hexenyl, 1-ethyl-c-hexenyl, 1-c-heptenyl, 2-c-heptenyl, 3-c-heptenyl, 4-c-heptenyl, 1-c-octenyl, 2-c-octenyl, 3-c-octenyl, 4-c-octenyl or the like may be mentioned.

A $C_{1-6}$ alkylcarbonyl group may be linear, branched or cyclic, and methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

As a $C_{1-7}$ acyl group, a formyl group may be mentioned in addition to the above $C_{1-6}$ alkylcarbonyl groups.

A $C_{1-10}$ alkylcarbonyl group may be linear, branched or a $C_{3-10}$ cycloalkylcarbonyl group, and in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{2-9}$ heterocyclyl group may be a heteromonocyclic or fused heterobicyclic group consisting of at least one atom selected from the group consisting of nitrogen atoms, oxygen atoms and sulfur atoms and from 2 to 9 carbon atoms. Specifically, the following examples are mentioned:

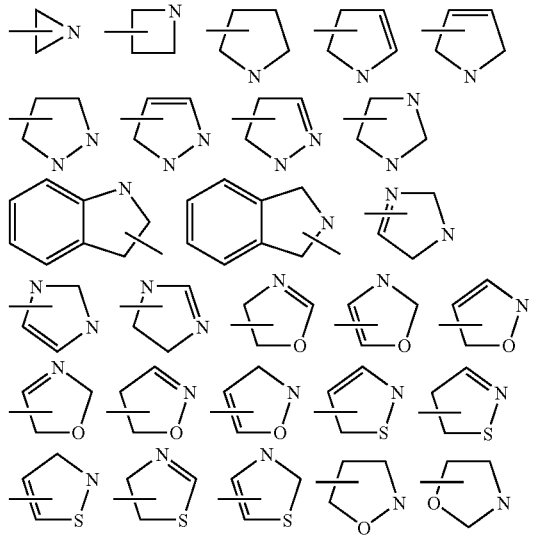

-continued

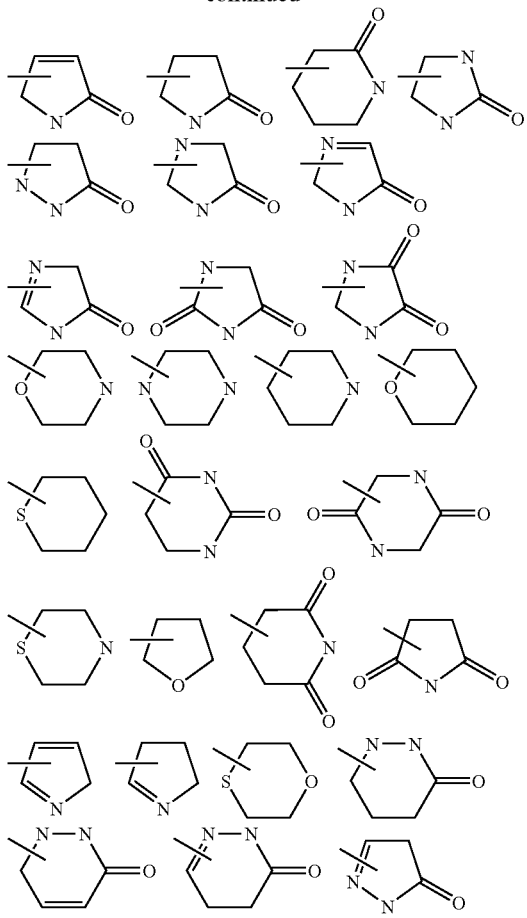

A C$_{2-14}$ aryl group may be a C$_{6-14}$ aryl group containing no hetero atoms as ring constituting atoms or a C$_{2-9}$ aromatic heterocyclic group. A C$_{2-9}$ aromatic heterocyclic group may be a 5 to 7-membered C$_{2-6}$ heteromonocyclic group or 8 to 10-membered C$_{5-9}$ fused heterobicyclic group containing from 1 to 3 atoms selected from the group consisting of oxygen atoms, nitrogen atoms and sulfur atoms singly or in combination.

A C$_{6-14}$ aryl group containing no hetero atoms may be a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like.

A 5 to 7-membered C$_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered C$_{5-9}$ fused heterobicyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pterdinyl group, a 4-pterdinyl group, a 6-pterdinyl group, a 7-pterdinyl group or the like.

A C$_{2-14}$ aryloxy group may be a C$_{6-14}$ aryloxy group containing no hetero atoms as ring constituting atoms or a C$_{2-9}$ aromatic heterocyclyloxy group, and a C$_{2-9}$ aromatic heterocyclyloxy group may be a 5 to 7-membered C$_{2-6}$ monocyclic heterocyclyloxy group or 8 to 10-membered C$_{5-9}$ fused bicyclic heterocyclyloxy group containing from 1 to 3 oxygen atoms, nitrogen atoms or sulfur atoms singly or in combination.

A $C_{6-14}$ aryloxy group containing no hetero atoms may be a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like.

A 5 to 7-membered $C_{2-6}$ monocyclic heterocyclyloxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused bicyclic heterocyclyloxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pterdinyloxy group, a 4-pterdinyloxy group, a 6-pterdinyloxy group, a 7-pterdinyloxy group or the like.

A $C_{1-10}$ alkoxy group may be linear, branched or a $C_{3-10}$ cycloalkoxy group, and methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-10}$ thioalkyl group may be linear, branched or a $C_{3-10}$ cyclothioalkyl group, and methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentylthio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3-ethyl-2,2-dimethyl-3-n-pentylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-6}$ alkoxycarbonyl group may be linear, branched or a $C_{3-6}$ cycloalkoxycarbonyl group, and methoxycarbonyl, ethoxycarbonyl, n-propoxycarbonyl, i-propoxycarbonyl, c-propoxycarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and in addition to those mentioned above, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonylxoy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propycarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propylcarbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, i-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A $C_{1-10}$ dialkylamino group may be symmetric or asymmetric. A symmetric $C_{1-10}$ dialkylamino group may be linear, branched or a $C_{3-10}$ cycloalkylamino group, and dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c- propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric $C_{1-10}$ dialkylamino group may be linear, branched or a $C_{3-10}$ cycloalkylamino group, and (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, C-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)amino, (n-hexyl, c-hexyl)amino, (methyl, n-heptyl)amino, (methyl, n-octyl)amino, (methyl, n-nonyl)amino, (methyl, n-decyl)amino, (methyl, n-heptyl)amino, (ethyl, n-octyl)amino, (ethyl, n-nonyl)amino, (ethyl, n-decyl)amino or the like may be mentioned.

A $C_{1-6}$ alkylsulfonyl group may be linear, branched or a $C_{3-6}$ cycloalkylsulfonyl group, and methylsulfonyl, ethylsulfonyl, n-propylsulfonyl, i-propylsulfonyl, c-propylsulfonyl, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl or the like may be mentioned.

A $C_{1-10}$ alkylsulfonyl group may be linear, branched or a $C_{3-10}$ cycloalkylsulfonyl group, and in addition to those mentioned above, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-heptylsulfonyl, 2,4,4-trimethyl-1-n-pentylsulfonyl, 1-nonylsulfonyl, 2-nonylsulfonyl, 2,6-dimethyl-4-n-heptylsulfonyl, 3-ethyl-2,2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl, c-heptylsulfonyl, c-octylsulfonyl, 1-methyl-c-hexylsulfonyl, 2-methyl-c-hexylsulfonyl, 3-methyl-c-hexylsulfonyl, 1,2-dimethyl-c-hexylsulfonyl, 1-ethyl-c-hexylsulfonyl, 1-methyl-c-pentylsulfonyl, 2-methyl-c-pentylsulfonyl, 3-methyl-c-pentylsulfonyl or the like may be mentioned.

The protecting group in a protected hydroxyl group, a protected thiol group, a protected amino group, a protected tetrazole group, a protected phosphonic acid group and a protected sulfonic acid group may be a $C_{1-4}$ alkoxymethyl group (such as a MOM (methoxymethyl) group, a MEM (2-methoxyethoxymethyl) group, an ethoxymethyl group, a n-propoxymethyl group, an i-propoxymethyl group, a n-butoxymethyl group, an iBM (isobutyloxymethyl) group, a BUM (t-butoxymethyl) group, a POM (pivaloyloxymethyl) group, a SEM (trimethylsilylethoxymethyl) group and the like, preferably a MOM (methoxymethyl) group, a MEM (2-methoxyethoxymethyl) group, a POM (pivaloyloxymethyl) group or the like), an aryloxymethyl group (such as a BOM (benzyloxymethyl) group, a PMBM (p-methoxybenzyloxymethyl) group, a p-AOM (p-anisyloxymethyl) group and the like, preferably a benzyloxymethyl group), a $C_{1-4}$ alkylaminomethyl group (such as a dimethylaminomethyl group), a substituted acetamidomethyl group (such as an Acm (acetamidomethyl) group, a Tacm (trimethylacetamidomethyl) group and the like), a substituted thiomethyl group (such as a MTM (methylthiomethyl) group, a PTM (phenylthiomethyl) group, a Btm (benzylthiomethyl) group and the like), a carboxyl group, a $C_{1-7}$ acyl group (such as a formyl group, an acetyl group, a fluoroacetyl group, a difluoroacetyl group, a trifluoroacetyl group, a chloroacetyl group, a dichloroacetyl group, a trichloroacetyl group, a propionyl group, a Pv (pivaloyl) group, a tigloyl group and the like), an arylcarbonyl group (such as a benzoyl group, a p-bromobenzoyl group, a p-nitrobenzoyl group, a 2,4-dinitrobenzoyl group, a benzoylformyl group, a benzoylpropionyl group, a 3-phenylpropionyl group and the like), a $C_{1-4}$ alkoxycarbonyl group (such as a methoxycarbonyl group, an ethoxycarbonyl group, a n-propoxycarbonyl group, an i-propoxycarbonyl group, a n-butoxycarbonyl group, an i-butoxycarbonyl group, a BOC (t-butoxycarbonyl group), an AOC (t-amyloxycarbonyl) group, a VOC (vinyloxycarbonyl) group, an AOC (allyloxycarbonyl) group, a Teoc (2-(trimethylsilyl)ethoxycarbonyl) group, a Troc (2,2,2-trichloroethoxycarbonyl) group and the like, preferably a BOC group and the like), an aryloxycarbonyl group (such as a Z (benzyloxycarbonyl) group, a p-nitrobenzyloxycarbonyl group, a MOZ (p-methoxybenzyloxycarbonyl) group and the like), a $C_{1-4}$ alkylaminocarbonyl group (such as a methylcarbamoyl group, an Ec (ethylcarbamoyl) group, a n-propylcarbamoyl group and the like), an arylaminocarbonyl group (such as a phenylcarbamoyl group and the like), a trialkylsilyl group (such as a TMS (trimethylsilyl) group, a TES (triethylsilyl) group, a TIPS (triisopropylsilyl) group, a DEIPS (diethylisopropylsilyl) group, a DMIPS (dimethylisopropylsilyl) group, a DTBMS (di-t-butylmethylsilyl) group, an IPDMS (isopropyldimethylsilyl) group, a TBDMS (t-butyldimethylsilyl) group, a TDS (thexyldimethylsilyl) group and the like, preferably a TBDMS (t-butyldimethylsilyl) group and the like), a trialkylarylsilyl group (such as a DPMS (diphenylmethylsilyl) group, a TBDPS (t-butyldiphenylsilyl) group, a TBMPS (t-butyldimethoxyphenylsilyl) group, a TPS (triphenylsilyl) group and the like), an alkylsulfonyl group (such as a Ms (methanesulfonyl) group, an ethanesulfonyl group, a benzylsulfonyl group and the like) or an arylsulfonyl group (such as a benzenesulfonyl group, a Ts (p-toluenesulfonyl) group, a p-chlorobenzenesulfonyl group, a MBS (p-methoxybenzenesulfonyl) group, a m-nitrobenzenesulfonyl group, an iMds (2,6-dimethoxy-4-methylbenzenesulfonyl) group, a Mds (2,6-dimethyl-4-methoxybenzenesulfonyl) group, a Mtb (2,4,6-trimethoxybenzenesulfonyl) group, a Mte (2,3,5,6-tetramethyl-4-methoxybenzenesulfonyl) group, a Mtr (2,3,6-trimethyl-4-methoxybenzenesulfonyl) group, a Mts (2,4,6-trimethylbenzenesulfonyl) group, a Pme (pentamethylbenzenesulfonyl) group and the like), and a triphenylmethyl group (a trityl group) and the like.

In addition, a 1-methyl-1-methoxyethyl group, a 1-ethoxyethylgroup, a 2,2,2-trichloroethyl group, a 2-trimethylsilylethoxy group, a t-butyl group, an allyl group, a benzyl group, a p-methoxybenzyl group, a 2,4-dinitrophenyl group, a p-chlorophenyl group, a p-methoxyphenyl group, a tetrahydropyranyl group, a tetrahydrofuranyl group or the like may be mentioned.

Specific preferred examples of the substituent $R^1$ are a methyl group, an ethyl group, a n-propyl group, an i-propyl group, a n-butyl group, a s-butyl group, a t-butyl group, a c-propyl group, a c-butyl group, a c-pentyl group, a c-hexyl group, a phenyl group, a thienyl group (a 2-thienyl group, a 3-thienyl group), a furyl group (a 2-furyl group, a 3-furyl group) and a pyridyl group (a 2-pyridyl group, a 3-pyridyl group, a 4-pyridyl group) (each of the phenyl group, thienyl group, furyl group and pyridyl group may be substituted by a $C_{1-6}$ alkyl group).

Particularly preferred specific examples are a methyl group, an ethyl group, a n-propyl group, a n-butyl group, a c-hexyl group, a phenyl group and a p-methylphenyl group.

Specific preferred examples of the substituent $R^2$ are a phenyl group, a thienyl group (a 2-thienyl group, a 3-thienyl group), a furyl group (a 2-furyl group, a 3-furyl group), a pyridazinyl group (a 3-pyridazinyl group, a 4-pyridazinyl group), a pyridyl group (a 2-pyridyl group, a 3-pyridyl group, a 4-pyridyl group), a quinolyl group (a 2-quinolyl group, a 3-quinolyl group, a 4-quinolyl group, a 5-quinolyl group, a 6-quinolyl group, a 7-quinolyl group, a 8-quinolyl group), an isoquinolyl group (a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group) and the following heterocyclyl groups (each of the phenyl group, thienyl group, furyl group, pyridazinyl group, pyridyl group, quinolyl group, isoquinolyl group and heterocyclyl group may optionally be substituted by a protected hydroxyl group, a protected thiol group, a protected amino group, a $C_{1-6}$ alkoxy group, a mono- or di-$C_{1-6}$ alkylamino group, a $C_{1-6}$ thioalkyl group, a $C_{1-6}$ alkoxycarbonyl group, a phosphonic acid $C_{1-6}$ alkyl ester group, a protected phosphonic acid group, a sulfonic acid $C_{1-6}$ alkyl ester group, a protected sulfonic acid group, —CH$_2$CO$_2$Me, —OCH$_2$CO$_2$Me, —NHCH$_2$CO$_2$Me, —CH$_2$CH$_2$CO$_2$Me, —NHCH$_2$CH$_2$CO$_2$Me, a $C_{1-10}$ alkyl group, a $C_{2-10}$ alkenyl group, a $C_{2-10}$ alkynyl group, the following heterocyclyl groups, a $C_{1-10}$ alkoxy group, a $C_{1-10}$ thioalkyl group, a $C_{1-10}$ alkylcarbonyl group, a mono- or di-$C_{1-10}$ alkylamino group, a $C_{1-10}$ alkylcarbonyloxy group, a $C_{1-10}$ alkoxycarbonyl group, a $C_{1-10}$ alkylcarbonylamino group, a phenyl group, a thienyl group (a 2-thienyl group, a 3-thienyl group), a furyl group (a 2-furyl group, a 3-furyl group), a pyridazinyl group (a 3-pyridazinyl group, a 4-pyridazinyl group), a pyridyl group (a 2-pyridyl group, a 3-pyridyl group, a 4-pyridyl group), a quinolyl group (a 2-quinolyl group, a 3-quinolyl group, a 4-quinolyl group, a 5-quinolyl group, a 6-quinolyl group, a 7-quinolyl group, a 8-quinolyl group), an isoquinolyl group (a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group), a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group or a 1,2-thiazole group (each of the $C_{1-10}$ alkyl group, $C_{2-10}$ alkenyl group, $C_{2-10}$ alkynyl group, heterocyclyl group, $C_{1-10}$ alkoxy group, $C_{1-10}$ thioalkyl group, $C_{1-10}$ alkylcarbonyl group, mono- or di-$C_{1-10}$ alkylamino group, $C_{1-10}$ alkylcarbonyloxy group, $C_{1-10}$ alkoxycarbonyl group, $C_{1-10}$ alkylcarbonylamino group, phenyl group, thienyl group (2-thienyl group, 3-thienyl group), furyl group (2-furyl group, 3-furyl group), pyridazinyl group (3-pyridazinyl group, 4-pyridazinyl group), pyridyl group (2-pyridyl group, 3-pyridyl group, 4-pyridyl group), quinolyl group (2-quinolyl group, 3-quinolyl group, 4-quinolyl group, 5-quinolyl group, 6-quinolyl group, 7-quinolyl group, 8-quinolyl group), isoquinolyl group (1-isoquinolyl group, 3-isoquinolyl group, 4-isoquinolyl group, 5-isoquinolyl group, 6-isoquinolyl group, 7-isoquinolyl group, 8-isoquinolyl group), 1,3,4-oxadiazole group, 1,3,4-thiadiazole group, 1,2,4-oxadiazole group, 1,2,4-thiadiazole group, 1,2,5-oxadiazole group, 1,2,5-thiadiazole group, 1,2-oxazole group and 1,2-thiazole group may optionally be substituted by a phosphonic acid $C_{1-6}$ alkyl ester group, a protected phosphonic acid group, a sulfonic acid $C_{1-6}$ alkyl ester group, a protected sulfonic acid group, —CH$_2$CO$_2$Me, —OCH$_2$CO$_2$Me, —NHCH$_2$CO$_2$Me, —CH$_2$CH$_2$CO$_2$Me, —NHCH$_2$CH$_2$CO$_2$Me, a $C_{1-10}$alkylcarbonyloxy group, a hydroxyl group protected by a protecting group, a protected thiol group, a protected amino group, a $C_{1-10}$ alkoxy group, a mono- or di-$C_{1-10}$ alkylamino group, a $C_{1-10}$ thioalkyl group or a $C_{1-6}$ alkoxycarbonyl group)).

The following examples are mentioned as the heterocyclyl group:

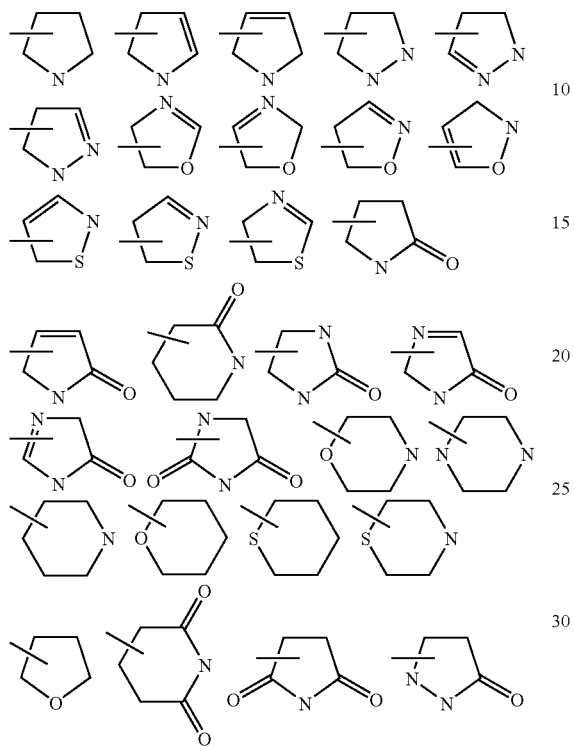

Preferred examples of $R^3$ are a carbamoyl group, an isonitrile group, an isocyanate group, a formylamino group, and $NHCO_2$ t-Bu.

Favorable compounds as the α-substituted vinyltin compound of the present invention are as follows.

1) E-form compounds represented by the formula (1) wherein $R^1$ is n-butyl, $R^3$ is carbamoyl and $R^2$ has the following structure, tautomers or salts of the compounds or solvates thereof:

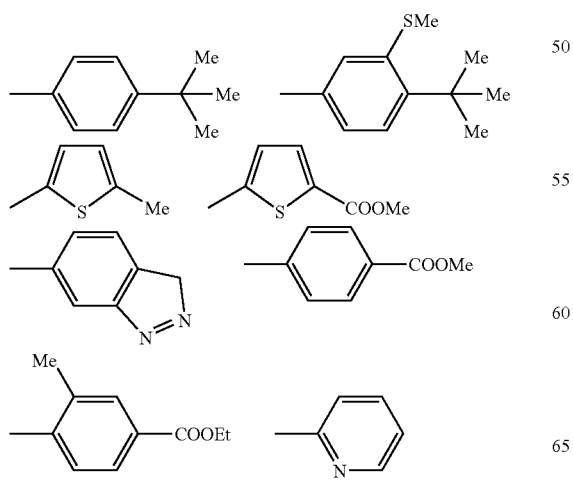

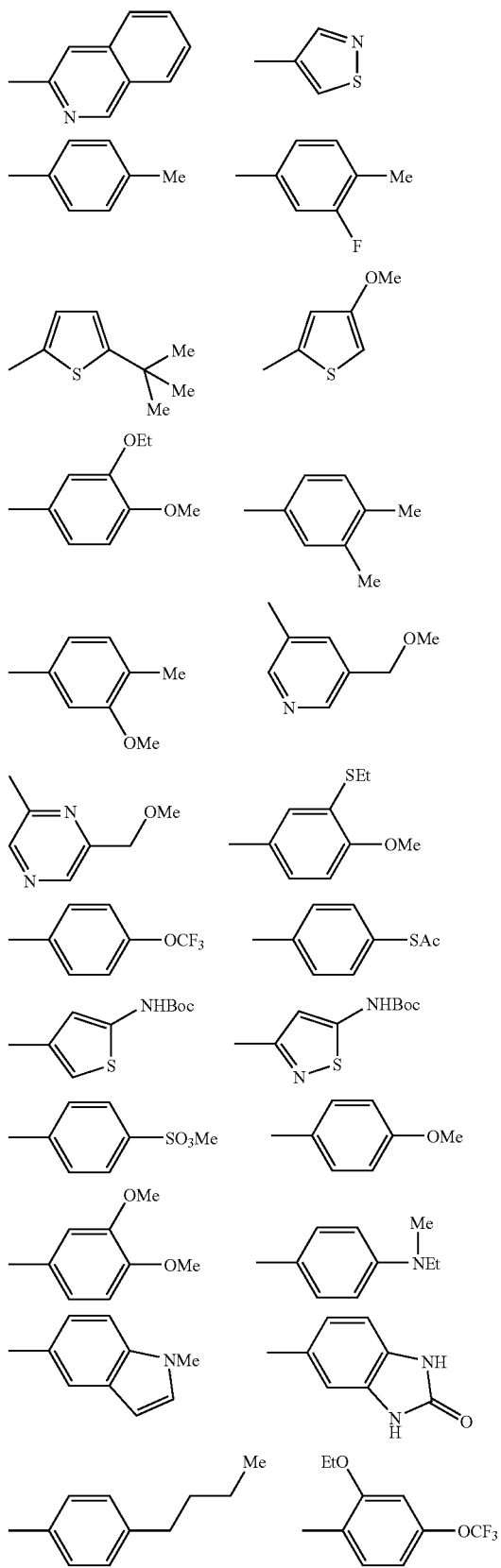

-continued
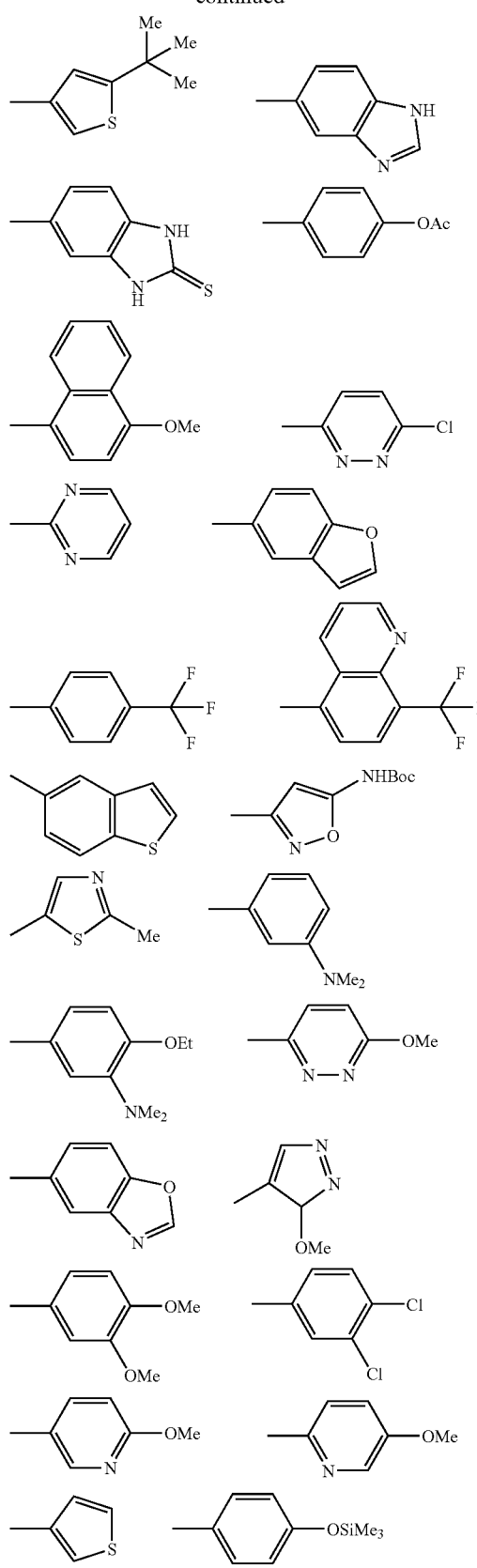
2) E-form compounds represented by the formula (1) wherein $R^1$ is n-butyl, $R^3$ is carbamoyl and $R^2$ has the following structure, tautomers or salts of the compounds or solvates thereof:
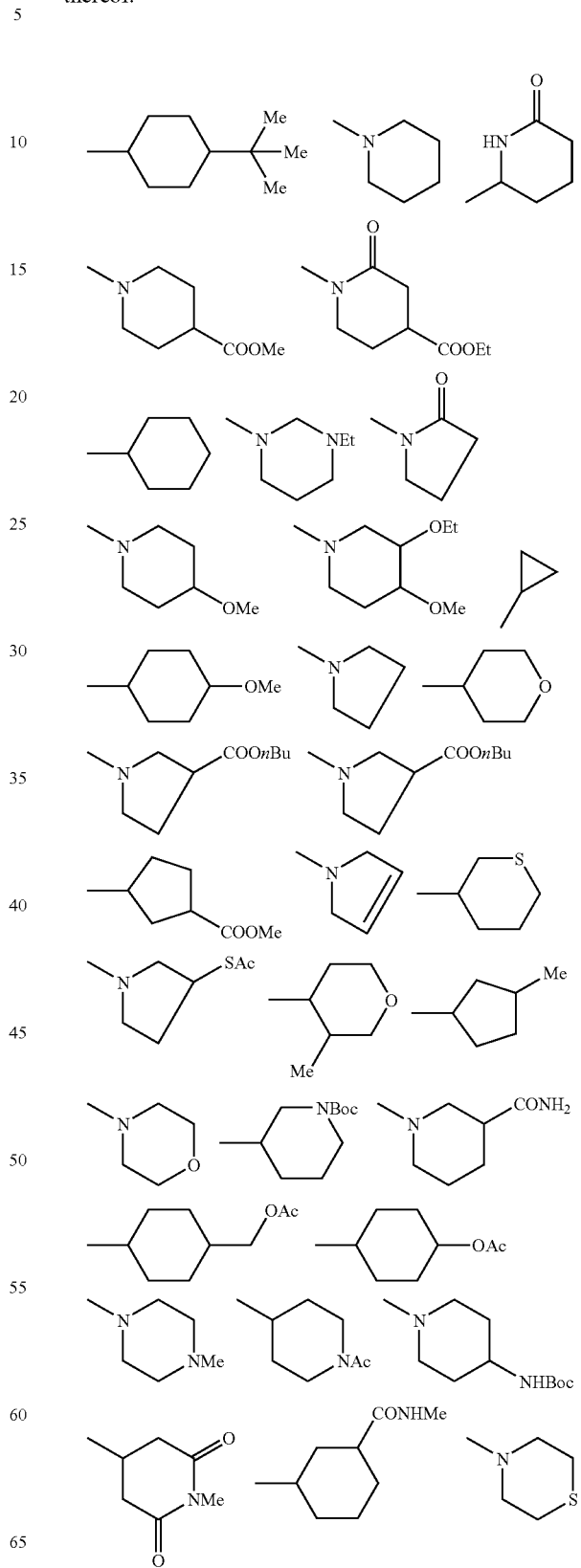

-continued

3) Z-form compounds represented by the formula (1) wherein R¹ is n-butyl, R³ is carbamoyl and R has the following structure, tautomers or salts of the compounds or solvates thereof:

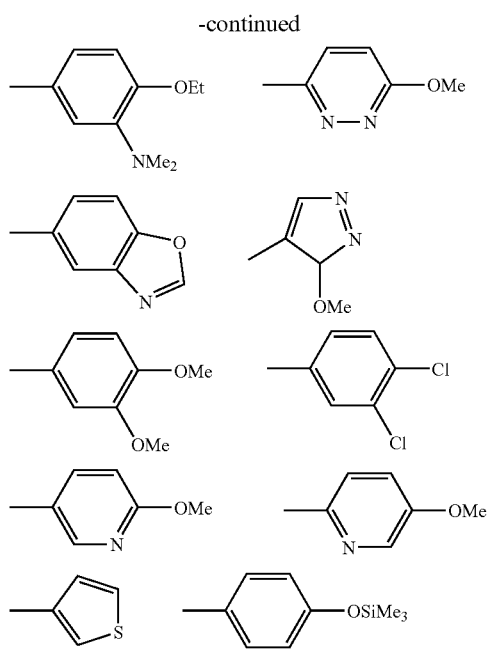

4) Z-form compounds represented by the formula (1) wherein $R^1$ is n-butyl, $R^3$ is carbamoyl and $R^2$ has the following structure, tautomers or salts of the compounds or solvates thereof:

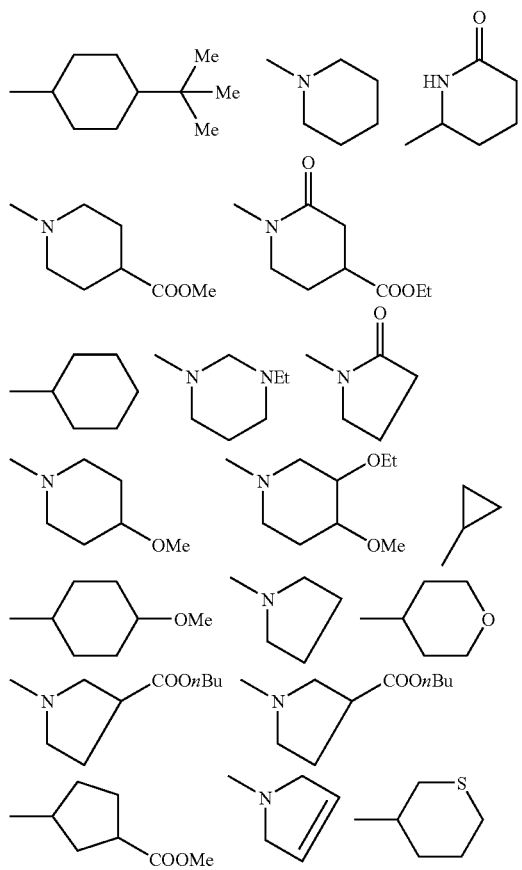

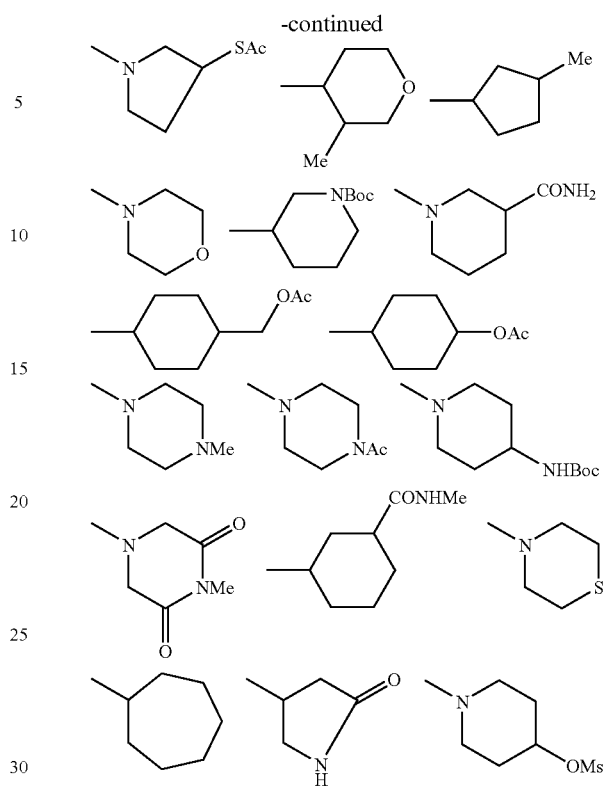

5) The compounds according to 1) to 4), wherein $R^1$ is converted to methyl, tautomers or salts of the compounds or solvates thereof.

6) The compounds according to 1) to 4), wherein $R^1$ is converted to phenyl, tautomers or salts of the compounds or solvates thereof.

7) The compounds according to 1) to 4), wherein $R^1$ is converted to p-methylphenyl, tautomers or salts of the compounds or solvates thereof.

8) The compounds according to 1) to 4), wherein $R^1$ is converted to cyclohexyl, tautomers or salts of the compounds or solvates thereof.

9) The compounds according to 1) to 8), wherein $R^3$ is converted to thiocarbamoyl, tautomers or salts of the compounds or solvates thereof.

10) The compounds according to 1) to 8), wherein $R^3$ is converted to isonitrile, tautomers or salts of the compounds or solvates thereof.

11) The compounds according to 1) to 8), wherein $R^3$ is converted to isocyanate, tautomers or salts of the compounds or solvates thereof.

12) The compounds according to 1) to 8), wherein $R^3$ is converted to isothiocyanate, tautomers or salts of the compounds or solvates thereof.

13) The compounds according to 1) to 8), wherein $R^3$ is converted to formylamino, tautomers or salts of the compounds or solvates thereof.

14) The compounds according to 1) to 8), wherein $R^3$ is converted to thioformylamino, tautomers or salts of the compounds or solvates thereof.

15) The compounds according to 1) to 8), wherein $R^3$ is converted to the following structure, tautomers or salts of the compounds or solvates thereof:

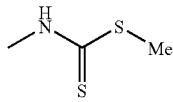

16) The compounds according to 1) to 8), wherein $R^3$ is converted to the following structure, tautomers or salts of the compounds or solvates thereof:

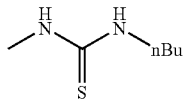

17) The compounds according to 1) to 8), wherein $R^3$ is converted to the following structure, tautomers or salts of the compounds or solvates thereof:

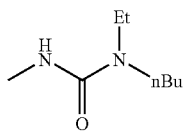

18) The compounds according to 1) to 8), wherein $R^3$ is converted to the following structure, tautomers or salts of the compounds or solvates thereof:

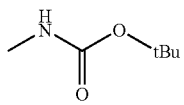

The compounds of the present invention represented by the formula (1) or acceptable salts thereof may be in the form of arbitrary crystals or arbitrary hydrates, depending on the production conditions. The present invention covers these crystals, hydrates and mixtures thereof. They may be in the form of solvates with organic solvents such as acetone, ethanol and tetrahydrofuran, and the present invention covers any of these forms.

The compounds of the present invention represented by the formula (1) may be converted to acceptable salts or may be liberated from the resulting salts, if necessary. The acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid).

EXAMPLES

Now, the present invention will be described in further detail with reference to Reference Synthetic Examples and Synthetic Examples. However, it should be understood that the present invention is by no means restricted by these specific Examples.

Reference Synthetic Example 1

Synthesis of 1-(2,2-dibromovinyl)-4-methoxybenzene

Triphenylphosphine (57.8 g, 220 mmol) was dissolved in dichromomethane (200 ml) in nitrogen atmosphere, and carbon tetrabromide (36.5 g, 110 mmol) was added little by little under cooling with ice, followed by stirring for 30 minutes. Then, p-anisic aldehyde (10.0 g, 73.4 mmol) was dropwise added under cooling with ice, followed by stirring for 10 minutes. The reaction solution was subjected to filtration, silica gel (50 g) was added to the filtrate, and the filtrate was concentrated under reduced pressure to dryness, and the resulting product was purified by silica gel column chromatography (hexane:ethyl acetate=20:1) to give the desired compound 1-(2,2-dibromovinyl)-4-methoxybenzene (21.4 g, quant.) as pale yellow solid.

Melting point (morphology): 36° C. (white solid) LRFAB-MS (m/z): 291.9, 289.1 [M+H]$^+$; calculated value $C_9H_8Br_2O$: 291.9, 289.9. $^1$H-NMR (ppm, 400 MHz, CDCl$_3$) δ 7.52 (2H, d, J=8.8 Hz), 7.41 (1H, s), 6.90 (2H, d, J=8.8 Hz), 3.86 (3H, s). $^{13}$C-NMR (ppm, 100 MHz, CDCl$_3$) δ159.5, 136.2, 129.8, 127.7, 113.7, 87.2, 55.3.

Reference Synthetic Example 2

Synthesis of (4-methoxyphenyl)propionic acid 1-(2,2-dibromovinyl)-4-methoxybenzene (17.38 g, 59.5 mmol) prepared in Reference Synthetic Example 1 was dissolved in tetrahydrofuran (230 ml) in nitrogen atmosphere, and a 2.59 mol/l n-butyllithium/hexane solution was dropwise added at −78° C. After the dropwise addition, the solution was returned to 0° C. and stirred for 90 minutes, and then cooled to −78° C. again, and crushed dry ice was added. After stirring for 30 minutes, water was added to the solution and the solution was concentrated under reduced pressure. The residue was diluted with diethyl ether, and extracted with a 1 mol/l sodium hydroxide aqueous solution twice. The obtained aqueous layer was acidified (pH=1) with hydrochloric acid and extracted with ethyl acetate twice. The obtained organic layer was washed with water and a saturated salt solution, dried over anhydrous sodium sulfate, subjected to filtration and concentrated under reduced pressure to give the desired compound (4-methxoyphenyl)propionic acid (9.73 g, 93%) as crude crystals.

Melting point (morphology): 140° C. (decomposed, colorless crystals) LRFAB-MS (m/z): 177.1 [M+H]$^+$; calculated value $C_{10}H_8O_3$: 176.0.

$^1$H-NMR (ppm, 400 MHz, CDCl$_3$): δ7.57 (2H, d, J=8.8 Hz), 6.91 (2H, d, J=8.8 Hz), 3.85 (3H, s).
$^{13}$C-NMR (ppm, 100 MHz, CDCl$_3$): δ161.8, 158.4, 135.3, 114.3, 110.8, 90.0, 79.6, 55.5.

Reference Synthetic Example 3

Synthesis of (3-(4-methoxyphenyl)propionic acid amide (4-methoxyphenyl)propionic acid (20.0 mg, 0.11 mmol) prepared in Reference Synthetic Example 2 was dissolved in tetrahydrofuran (500 μl) in nitrogen atmosphere, and triethylamine (17 µl, 0.12 mmol) and ethyl chloroformate (11 µl, 0.12 mmol) were dropwise added under cooling with ice, followed by stirring for 15 minutes. A 28% ammonia aqueous solution was dropwise added, followed by stirring for 5 minutes, and the reaction solution was poured into water and extracted with ethyl acetate. The organic layer was concentrated under reduced pressure, and the residue was purified by silica gel column chromatography (hexane:ethyl acetate=3:2 to 1:2) to give the desired compound 3-(4-methoxyphenyl) propionic acid amide (18.9 mg, 95%) as colorless needle crystals.

Melting point (morphology): 153° C. (colorless needle crystals) LRFAB-MS (m/z): 176.1 [M+H]$^+$; calculated value $C_{10}H_9NO_2$: 175.1.

$^1$H-NMR (ppm, 400 MHz, CDCl$_3$): δ7.50 (2H, d, J=8.8 Hz), 6.88 (2H, d, J=8.8 Hz), 5.80 (2H, br.s), 3.84 (3H, s).

$^{13}$C-NMR (ppm, 100 MHz, CDCl$_3$): δ161.1, 155.0, 134.4, 114.2, 111.7, 86.7, 81.5, 55.4

Synthetic Example 1

Synthesis of (E)-2-{tri(n-butyl)stannyl}-3-(4-methoxyphenyl)acrylamide 3-(4-methoxyphenyl)propionic acid amide (10.3 mg, 0.059 mmol) prepared in Reference Synthetic Example 3 was dissolved in tetrahydrofuran (500 µl) in nitrogen atmosphere, tetrakistriphenylphosphine palladium (1.4 mg, 0.0012 mmol) was added under cooling with ice, and a tetrahydrofuran solution of tri-n-butyltin hydride (20 µl, 0.074 mmol) was dropwise added. After stirring for 10 minutes, the solution was concentrated under reduced pressure, and the residue was purified by silica gel column chromatography (hexane:ethyl acetate=3:1) to give the desired compound (E)-2-{tri(n-butyl) stannyl}-3-(4-methoxyphenyl)acrylamide (18.6 mg, 68%) as a colorless oily substance.

LRFAB-MS (m/z): 468.2, 467.2 [M+H]$^+$; calculated value $C_{22}H_{37}NO_2Sn$: 467.2, 465.2.

$^1$H-NMR (ppm, 400 MHz, CDCl$_3$): δ7.38 (2H, d, J=8.8 Hz), 6.84 (2H, d, J=8.8 Hz), 6.58 (1H, s, $J_{Sn-H}$=30.4 Hz), 5.25 (1H, br.s), 5.21 (1H, br.s), 3.80 (3H, s), 1.56 (6H, m), 1.35 (6H, m), 1.07 (6H, m), 0.91 (9H, t, J=7.2 Hz).

$^{13}$C-NMR (ppm, 100 MHz, CDCl$_3$): δ176.1, 159.3, 141.0, 139.1, 129.6, 129.3, 113.7, 55.3, 29.0, 27.3, 13.7, 10.5.

Synthetic Example 2

Synthesis of [(E)-1-{tri(n-butyl)stannyl}-2-(4-methoxyphenyl)]vinyl isocyanate (E)-2-{tri(n-butyl)stannyl}-3-(4-methoxyphenyl)acrylamide (130.2 mg, 0.28 mmol) prepared in the same manner as in Synthetic Example 1 was dissolved in tetrahydrofuran (2.8 ml) in nitrogen atmosphere, and lead tetraacetate (136.2 mg, 0.31 mmol) was added at room temperature. After stirring for 30 minutes, the reaction solution was subjected to filtration with Celite, and the filtrate was concentrated under reduced pressure. The residue was purified by silica gel column chromatography (hexane:ethyl acetate=20:1) to give the desired compound [(E)-1-{tri(n-butyl)stannyl}-2-(4-methoxyphenyl)]vinyl isocyanate (114.1 mg, 88%) as a pale yellow oily substance. IR (film): 2,206 cm$^{-1}$ (—NCO).

$^1$H-NMR (ppm, 400 MHz, CDCl$_3$): δ7.60 (2H, d, J=8.8 Hz), 6.88 (2H, d, J=8.8 Hz), 5.89 (1H, s, $J_{Sn-H}$=16.8 Hz), 3.81 (3H, s), 1.57 (6H, m), 1.36 (6H, m), 1.10 (6H, m), 0.91 (9H, t, J=7.2 Hz).

$^{13}$C-NMR (ppm, 100 MHz, CDCl$_3$): δ158.8, 133.4, 130.6, 129.6, 128.4, 124.6, 113.6, 55.3, 28.9, 27.3, 13.7, 10.6.

Synthetic Example 3

Synthesis of N-[(E)-1-{tri(n-butyl)stannyl}-2-(4-methoxyphenyl)vinyl]formamide

[(E)-1-{tri(n-butyl)stannyl}-2-(4-methoxyhenyl)]vinyl isocyanate (17.5 mg, 0.038 mmol) prepared in Synthetic Example 2 was dissolved in tetrahydrofuran (800 µl) in nitrogen atmosphere, and a 1.0 mol/l lithium triethylborohydride/ tetrahydrofuran solution (40 µl, 0.040 mmol) was dropwise added at −78° C. After stirring for 2 hours, 20 µl (0.020 mmol) of the solution was further added dropwise, followed by stirring for one hour. The reaction was terminated by a saturated ammonium chloride aqueous solution, silica gel was added, and the reaction solution was concentrated under reduced pressure to dryness, and the resulting product was purified by silica gel column chromatography (hexane:ethyl acetate=5:1) to give the aimed compound N-[(E)-1-{tri(n-butyl)stannyl}-2-(4-methoxyphenyl)vinyl]formamide (12.3 mg, 70%) as a pale yellow oily substance.

LRFAB-MS (m/z): 468.1, 466.1 [M+H]$^+$; calculated value $C_{22}H_{37}NO_2Sn$: 467.2, 465.2.

Main Component $^1$H-NMR (ppm, 400 MHz, CDCl$_3$): δ8.10 (1H, br.s), 7.87 (1H, br.s), 7.19 (2H, d, J=8.8 Hz), 6.92 (2H, d, J=8.8 Hz), 5.92 (1H, s, $J_{Sn-H}$=20.8 Hz), 3.82 (3H, s), 1.53 (6H, m), 1.34 (6H, m), 1.00 (6H, m), 0.90 (9H, t, J=7.2 Hz).

$^{13}$C-NMR (ppm, 100 MHz, CDCl$_3$): δ159.1, 158.3, 135.4, 129.3, 128.6, 122.5, 114.4, 55.3, 29.1, 27.4, 13.9, 12.2.

Accessory Component $^1$H-NMR (ppm, 400 MHz, CDCl$_3$): δ8.38 (1H, d, J=11.6 Hz), 7.87 (1H, br.s), 7.17 (2H, d, J=8.8 Hz), 6.90 (2H, d, J=8.8 Hz), 5.75 (1H, s), 3.82 (3H, s), 1.53 (6H, m), 1.34 (6H, m), 1.09 (6H, m), 0.92 (9H, t, J=7.2 Hz).

Synthetic Example 4

Synthesis of (Z)-2-{tri(n-butyl)stannyl}-3-(4-methoxyphenyl)acrylamide 3-(4-methoxyhenyl)propionic acid amide (1.92 g, 11.0 mmol) prepared in the same manner as in Reference Synthetic Example 3 was dissolved in tetrahydrofuran (110 ml) in nitrogen atmosphere, and tri(n-butyl)tin hydride (3.8 ml, 14.1 mmol) and 2,2'-azobisisobutyronitrile (36.1 mg, 0.22 mol) were added under cooling with ice, followed by stirring for 20 hours. Carbon tetrachloride and potassium fluoride were added, followed by stirring further for one hour, the reaction solution was subjected to filtration, and the filtrate was concentrated under reduced pressure. The residue was purified by silica gel column chromatography (hexane:ethyl acetate=4:1 to 1:2) to give the desired compound (Z)-2-{tri(n-butyl)stannyl}-3-(4-methoxyphenyl)acrylamide (2.37 g, 46%) as colorless needle crystals. In addition, compound (E)-2-{tri(n-butyl)stannyl}-3-(4-methoxyphenyl)acrylamide (0.33 g, 6%) as a colorless oily substance and the starting material 3-(4-methoxyphenyl)propionic acid amide (0.48 g, 25%) were recovered.

Melting point (morphology): 59° C. (colorless needle crystals) LRFAB-MS (m/z): 468.1, 466.1 [M+H]$^+$; calculated value $C_{22}H_{37}NO_2Sn$: 467.2, 465.2.

$^1$H-NMR (ppm, 400 MHz, CDCl$_3$): δ7.33 (1H, s, $J_{Sn-H}$=52.0 Hz), 7.20 (2H, d, J=8.8 Hz), 6.87 (2H, d, J=8.8

Hz), 5.64 (2H, br.s), 3.82 (3H, s), 1.39 (6H, m), 1.24 (6H, m), 0.89 (6H, m), 0.83 (9H, t, J=7.2 Hz).

$^{13}$C-NMR (ppm, 100 MHz, CDCl$_3$): δ176.0, 159.7, 144.8, 143.1, 131.2, 129.0, 113.6, 55.4, 29.0, 27.3, 13.7, 11.8.

Synthetic Example 5

Synthesis of [(Z)-1-{tri(n-butyl)stannyl}-2-(4-methoxyphenyl)]vinyl isocyanate (Z)-2-{tri(n-butyl)stannyl}-3-(4-methoxyphenyl)acrylamide (1.09 g, 2.34 mmol) prepared in Synthetic Example 4 was dissolved in tetrahydrofuran (23 ml) in nitrogen atmosphere, and lead tetraacetate (1.15 g, 2.59 mmol) was added at room temperature. After stirring for 15 minutes, the reaction solution was subjected to filtration with Celite, and the filtrate was concentrated under reduced pressure. The residue was purified by silica gel column chromatography (hexane:ethyl acetate=20:1) to give the desired compound [(Z)-1-{tri(n-butyl)stannyl}-2-(4-methoxyphenyl)]vinyl isocyanate (0.98 g, 90%) as a pale yellow oily substance. IR (film): 2,267 cm$^{-1}$ (—NCO).

$^1$H-NMR (ppm, 400 MHz, CDCl$_3$): δ7.17 (1H, s), 7.08 (2H, d, J=8.8 Hz), 6.84 (2H, d, J=8.8 Hz), 3.81 (3H, s), 1.40 (6H, m), 1.26 (6H, m), 0.88 (6H, m), 0.86 (9H, t, J=7.2 Hz).

$^{13}$C-NMR (ppm, 100 MHz, CDCl$_3$): δ159.2, 138.2, 135.2, 130.0, 128.9, 121.8, 113.7, 55.3, 28.8, 27.2, 13.7, 11.5.

Synthetic Example 6

Synthesis of N-[(Z)-1-{tri(n-butyl)stannyl}-2-(4-methoxyphenyl)vinyl]formamide

[(Z)-1-{tri(n-butyl)stannyl}-2-(4-methoxyphenyl)]vinyl isocyanate (905.2 mg, 1.94 mmol) prepared in Synthetic Example 5 was dissolved in tetrahydrofuran (15 ml) in nitrogen atmosphere, and a 1.0 mol/l lithium triethylborohydride/tetrahydrofuran solution (3.0 ml, 3.0 mmol) was dropwise added at −78° C. After stirring for 2 hours, 1.0 ml (1.0 mmol) of the solution was further added dropwise, followed by stirring for 30 minutes. The reaction was terminated by ethyl acetate, and the reaction solution was poured into a saturated ammonium chloride aqueous solution and extracted with ethyl acetate twice. The organic layer put together was washed with water and a saturated salt solution and concentrated under reduced pressure. The residue was purified by silica gel column chromatography (hexane:ethyl acetate=5:1) to give the desired compound N-[(Z)-1-{tri(n-butyl)stannyl}-2-(4-methoxyphenyl)vinyl]formamide (715.2 mg, 79%) as a pale yellow oily substance.

LRFAB-MS (m/z): 468.1, 466.1 [M+H]$^+$; calculated value C$_{22}$H$_{37}$NO$_2$Sn: 467.1, 465.

Main Component $^1$H-NMR (ppm, 400 MHz, CDCl$_3$): δ8.11 (1H, br.s), 7.11 (2H, d, J=8.8 Hz), 7.04 (1H, s, J$_{Sn—H}$=41.6 Hz), 6.83 (2H, d, J=8.8 Hz), 3.81 (3H, s), 1.36 (6H, m), 1.20 (6H, m), 0.83 (9H, t, J=7.2 Hz), 0.76 (6H, m).

$^{13}$C-NMR (ppm, 100 MHz, CDCl$_3$): δ162.5, 159.0, 139.3, 130.7, 129.5, 129.4, 113.6, 55.3, 29.0, 27.3, 13.7, 12.8.

Accessory Component $^1$H-NMR (ppm, 400 MHz, CDCl$_3$): δ8.38 (1H, d, J=11.6 Hz), 7.10 (2H, d, J=8.8 Hz), 6.99 (1H, s, J$_{Sn—H}$=41.6 Hz), 6.85 (2H, d, J=8.8 Hz), 3.81 (3H, s) 1.36 (6H, m), 1.20 (6H, m,), 0.84 (9H, m), 0.76 (6H, m).

$^{13}$C-NMR (ppm, 100 MHz, CDCl$_3$): δ162.5, 158.9, 139.2, 130.5, 129.7, 129.3, 113.7, 55.3, 28.8, 27.2, 13.6, 11.4.

Reference Synthetic Example 4

Synthesis of 1,1'-[(1Z,3Z)-2,3-diformylamino-1,3-butadiene-1,4-diyl]bis[methoxybenzene]

N-[(E)-1-{tri(n-butyl)stannyl}-2-(4-methoxyphenyl)vinyl]formamide (142.5 mg, 0.31 mmol) prepared in the same manner as in Synthetic Example 3 was dissolved in tetrahydrofuran (3.1 ml) in nitrogen atmosphere, and palladium acetate (6.9 mg, 0.031 mmol) and copper(II) chloride (41.7 mg, 0.31 mmol) were added under cooling with ice, followed by stirring for 30 minutes. Triethylamine (86 μl, 0.62 mmol) and silica gel were added, and the reaction solution was concentrated under reduced pressure to dryness, and the resulting product was purified by silica gel column chromatography (toluene:acetone=4:1 to 3:2, containing 1% v/v triethylamine) to give the desired compound 1,1'-[(1Z,3Z)-2,3-diformylamino-1,3-butadiene-1,4-diyl]bis [methoxybenzene] (33.0 mg, 61%) as colorless solid.

Melting point (morphology): 219° C. (decomposed, colorless powder) LRFAB-MS (m/z): 352.2 M$^+$; calculated value C$_{20}$H$_{20}$N$_2$O$_4$: 352.1.

$^1$H-NMR (ppm, 400 MHz, DMSO-d$_6$): δ9.56 (br.s), 9.46 (br.s), 9.38 (d, J=10.8 Hz), 9.30 (d, J=10.8 Hz), 8.19 (m), 7.86 (d, J=10.8 Hz), 7.80 (d, J=10.8 Hz), 7.46 (m), 6.93 (m), 6.56 (s), 6.54 (s), 6.50 (s), 3.77 (s).

Reference Synthetic Example 5

Synthesis of 1,1'-[(1Z,3Z)-2,3-diisocyano-1,3-butadiene-1,4-diyl]bis[methoxybenzene] (xanthocillin X dimethyl ether)

1,1'-[(1Z,3Z)-2,3-diformylamino-1,3-butadiene-1,4-diyl]bis[methoxybenzene] (11.0 mg, 0.031 mmol) prepared in Reference Synthetic Example 4 was suspended in chloroform (200 μl) and pyridine (200 μl), and a dichloromethane solution of phosphorus oxychloride (6.4 μl, 0.069 mmol) was dropwise added under cooling with ice. After stirring for 45 minutes, the suspension was diluted with ethyl acetate, and poured into a saturated sodium hydrogen carbonate aqueous solution. Extraction with ethyl acetate was carried out twice, and the obtained organic layer was concentrated under reduced pressure. The residue was purified by silica gel column chromatography (hexane:ethyl acetate=5:1) to give the desired compound 1,1'-[(1Z,3Z)-2,3-diisocyano-1,3-butadiene-1,4-diyl]bis[methoxybenzene] (xanthocillin X dimethyl ether) (5.8 mg, 59%) as pale green crystals.

Melting point (morphology): 134° C. (decomposed, yellow crystals) LRFAB-MS (m/z): 316.1 M$^+$; calculated value C$_{20}$H$_{16}$N$_2$O$_2$: 316.1. IR (KBr): 2,117 cm$^{-1}$ (—NC).

$^1$H-NMR (ppm, 400 MHz, CDCl$_3$): δ7.79 (4H, d, J=8.8 Hz), 7.02 (2H, s), 6.99 (4H, d, J=8.8 Hz), 3.88 (6H, s).

$^{13}$C-NMR (ppm, 100 MHz, CDCl$_3$): δ173.1, 161.0, 131.6, 127.4, 124.8, 116.1, 114.4, 55.5.

Reference Synthetic Example 6

Synthesis of 1,1'-[(1E,3E)-2,3-diformylamino-1,3-butadiene-1,4-diyl]bis[methoxybenzene]

N-[(Z)-1-{tri(n-butyl)stannyl}-2-(4-methoxyphenyl)vinyl]formamide (34.0 mg, 0.073 mmol) prepared in Synthetic Example 6 was dissolved in tetrahydrofuran (730 μl) in nitrogen atmosphere, and palladium acetate (1.6 mg, 0.007 mmol) and copper(II) chloride (9.8 mg, 0.073 mmol) were added under cooling with ice, followed by stirring for 20 minutes. Triethylamine (20 μl, 0.14 mmol) and silica gel were added, and the solution was concentrated under reduced pressure to dryness, and the resulting product was purified by silica gel column chromatography (toluene:acetone=4:1 to 3:2, containing 1% v/v triethylamine) to give the desired compound 1,1'-[(1E,3E)-2,3-diformylamino-1,3-butadiene-1,4-diyl]bis[methoxybenzene] (33.0 mg, 61%) as pale yellow solid.

Melting point (morphology): 201° C. (decomposed, colorless powder) LRFAB-MS (m/z): 352.1 M$^+$; calculated value $C_{20}H_{20}N_2O_4$: 352.1

$^1$H-NMR (ppm, 400 MHz, DMSO-d$_6$): δ9.95 (d, J=10.8 Hz), 9.89 (d, J=10.8 Hz), 9.62 (br.s), 9.43 (br.s), 8.32 (d, J=10.8 Hz), 8.28 (d, J=10.8 Hz), 8.12 (br.s), 8.07 (br.s), 7.29 (s), 7.25 (m), 6.83 (m), 6.35 (s), 6.19 (s), 3.71 (s).

Reference Synthetic Example 7

Synthesis of 1,1'-[(1E,3E)-2,3-diisocyano-1,3-butadiene-1,4-diyl]bis[methoxybenzene]

1,1'-[(1E,3E)-2,3-diformylamino-1,3-butadiene-1,4-diyl]bis[methoxybenzene] (3.4 mg, 0.0096 mmol) prepared in Reference Synthetic Example 6 was suspended in chloroform (100 μl) and pyridine (100 μl), and a dichloromethane solution of phosphorus oxychloride (2 μl, 0.021 mmol) was dropwise added under cooling with ice. After stirring for 30 minutes, the suspension was diluted with ethyl acetate and poured into a saturated sodium hydrogen carbonate aqueous solution. Extraction with ethyl acetate was carried out twice, and the obtained organic layer was concentrated under reduced pressure. The residue was purified by silica gel column chromatography (hexane:ethyl acetate=3:1) to give the desired compound 1,1'-[(1E,3E)-2,3-diisocyano-1,3-butadiene-1,4-diyl]bis[methoxybenzene] (2.2 mg, 72%) as liver brown solid.

Melting point (morphology): 60° C. (decomposed, brown solid) LRFAB-MS (m/z): 317.1 [M+H]$^+$; calculated value $C_{20}H_{16}N_2O_2$: 316.1. IR (KBr): 2,102 cm$^{-1}$ (—NC)

$^1$H-NMR (ppm, 400 MHz, CDCl$_3$): δ7.34 (4H, d, J=8.8 Hz), 6.99 (2H, s), 6.85 (4H, d, J=8.8 Hz), 3.81 (6H, s).

$^{13}$C-NMR (ppm, 100 MHz, CDCl$_3$): δ163.8, 161.2, 136.7, 130.9, 128.0, 123.8, 114.3, 55.4.

Reference Synthetic Example 8

Synthesis of 3-(4-tert-butyldimethylsilyloxyphenyl)propionic acid amido

1) Synthesis of 4-(tert-butyldimethylsilyloxy)benzaldehyde 4-hydroxybenzaldehyde (8.21 g, 67.2 mmol) was dissolved in acetonitrile (164 ml) in nitrogen atmosphere, and imidazole (6.87 g, 100.8 mmol) was added at room temperature. Tert-butyldimethylsilyl chloride was added under cooling with ice, followed by stirring for 30 minutes. Methanol was added to terminate the reaction, the reaction solution was subjected to filtration, and the filtrate was concentrated under reduced pressure. The residue was purified by silica gel column chromatography (hexane:ethyl acetate=10:1) to give 4-(tert-butyldimethylsilyloxy)benzaldehyde (15.23 g, 96%) as a pale yellow oily substance.

LRFAB-MS (m/z): 236.2 M$^+$; calculated value $C_{13}H_{20}O_2Si$: 236.1.

$^1$H-NMR (ppm, 400 MHz, CDCl$_3$): δ9.87 (1H, s), 7.78 (2H, d, J=8.8 Hz), 6.90 (2H, d, J=8.8 Hz), 0.98 (9H, s), 0.24 (6H, s).

$^{13}$C-NMR (ppm, 100 MHz, CDCl$_3$): δ190.8, 161.5, 131.9, 130.4, 120.4, 25.5, 18.2, −4.5.

2) Synthesis of 1,1-dibromo-2-(tert-butyldimethylsilyloxyphenyl)ethylene

Triphenylphosphine (3.44 g, 13.1 mmol) was dissolved in dichloromethane (25 ml) in nitrogen atmosphere, carbon tetrabromide (2.18 g, 6.56 mmol) was added little by little under cooling with ice, and triethylamine (4.4 ml, 26.2 mmol) was dropwise added, followed by stirring for 10 minutes. Then, under cooling with ice, a dichloromethane solution (20 ml) of 4-(tert-butyldimethylsilyloxy)benzaldehyde (10.0 g, 73.4 mmol) prepared in 1) was dropwise added, followed by stirring for 1 hour. Silica gel (50 g) was added to the reaction solution, the reaction solution was concentrated under reduced pressure to dryness, and the resulting product was purified by silica gel column chromatography (hexane:ethyl acetate=20:1, containing 0.1% v/v triethylamine) to give 1,1-dibromo-2-(tert-butyldimethylsilyloxyphenyl)ethylene (2.77 g, 81%) as a pale yellow oily substance.

LRFAB-MS (m/z): 390.0, 392.0, 394.0 M$^+$; calculated value $C_{14}H_{20}Br_2OSi$: 390.0, 392.0, 394.0.

$^1$H-NMR (ppm, 400 MHz, CDCl$_3$): δ7.46 (2H, d, J=8.8 Hz), 7.40 (1H, s), 6.82 (2H, d, J=8.8 Hz), 0.98 (9H, s,), 0.21 (6H, s).

$^{13}$C-NMR (ppm, 75 MHz, CDCl$_3$): δ156.0, 136.4, 129.8, 128.3, 119.9, 87.2, 25.6, 18.2, −4.4.

3) 3-(4-tert-butyldimethylsilyloxyphenyl)propionic acid 1,1-dibromo-2-(tert-butyldimethylsilyloxyphenyl)ethylene (190.9 mg, 0.487 mmol) prepared in 2) was dissolved in tetrahydrofuran (2.9 ml) in nitrogen atmosphere, and a 1.58 mol/l n-butyllithium/hexane solution (832 μl, 1.31 mmol) was dropwise added at −78° C. After stirring for one hour, crushed dry ice was added to return the solution to 0° C. After stirring for 10 minutes, water was added, and the solution was concentrated under reduced pressure. The residue was diluted with diethyl ether and extracted with water. The obtained aqueous layer was acidified (pH=4) with a saturated potassium hydrogen sulfate aqueous solution and extracted with ethyl acetate. The obtained organic layer was washed with a saturated salt solution, dried over anhydrous sodium sulfate, subjected to filtration and concentrated under reduced pressure to give 3-(4-tert-butyldimethylsilyloxyphenyl)propionic acid (134.6 mg, quant.) as crude crystals.

LRFAB-MS (m/z): 277.2 [M+H]$^+$; calculated value $C_{15}H_{20}O_3Si$: 276.1.

$^1$H-NMR (ppm, 400 MHz, CDCl$_3$): δ7.51 (2H, d, J=8.8 Hz), 6.83 (2H, d, J=8.8 Hz), 0.98 (9H, s), 0.22 (6H, s).

$^{13}$C-NMR (ppm, 100 MHz, CDCl$_3$): δ161.4, 156.6, 135.0, 120.0, 113.6, 83.9, 83.7, 25.7, 18.2, −4.5.

4) 3-(4-tert-butyldimethylsilyloxyphenyl)propionic acid amide 3-(4-tert-butyldimethylsilyloxyphenyl)propionic acid (2.13 g, 7.71 mmol) prepared in 3) was dissolved in tetrahydrofuran (32 ml) in nitrogen atmosphere, and triethylamine (1.16 ml, 8.41 mmol) and ethyl chloroformate (0.726 ml, 8.41 ml) were dropwise added under cooling with ice, followed by stirring for 30 minutes. Then, a 28% ammonia aqueous solution was dropwise added, followed by stirring for 5 minutes. The reaction solution was concentrated under reduced pressure, and water was added to the residue, followed by extraction with ethyl acetate twice. The organic layer was concentrated under reduced pressure, and the residue was purified by silica gel column chromatography (hexane:ethyl acetate=2:1) to give 3-(4-tert-butyldimethylsilyloxyphenyl)propionic acid amide (1.60 g, 76%) as colorless solid.

Melting point (morphology): 97 to 98° C. (colorless solid)
LRFAB-MS (m/z): 276.2 [M+H]$^+$; calculated value $C_{15}H_{21}NO_2Si$: 275.1.
$^1$H-NMR (ppm, 400 MHz, CDCl$_3$): δ7.43 (2H, d, J=8.8 Hz), 6.81 (2H, d, J=8.8 Hz), 5.80 (2H, br.s), 0.98 (9H, s), 0.21 (6H, s).
$^{13}$C-NMR (ppm, 100 MHz, CDCl$_3$): δ157.8, 155.1, 134.4, 120.4, 112.4, 86.9, 81.7, 25.6, 18.2, 4.4.

Synthetic Example 7

Synthesis of (E)-2-(tributylstannyl)-3-(4-tert-butyldimethylsilyloxyphenyl)acrylamide 3-(4-tert-butyldimethylsilyloxyphenyl)propionic acid amide (1.13 g, 4.12 mmol) prepared in Reference Synthetic Example 8 was dissolved in tetrahydrofuran (23 ml) in nitrogen atmosphere, and tetrakistriphenylphosphine palladium (0) (95.2 mg, 0.082 mmol) was added under cooling with ice, and then a tetrahydrofuran solution (17 ml) of tri-n-butyltin hydride (5.2 ml, 19.3 mmol) was dropwise added. After stirring for 30 minutes, carbon tetrachloride was added to terminate the reaction, and potassium fluoride was added, followed by stirring for 30 minutes. After filtration, the filtrate was concentrated under reduced pressure, and the residue was purified by silica gel column chromatography (hexane:ethyl acetate=5:1) to give (E)-2-(tributylstannyl)-3-(4-tert-butyldimethylsilyloxyphenyl)acrylamide (1.51 g, 65%) as a pale yellow oily substance.

LRFAB-MS (m/z): 568.2, 566.2 [M+H]$^+$; calculated value $C_{27}H_{49}NO_2SiSn$: 567.3, 565.3.
$^1$H-NMR (ppm, 300 MHz, CDCl$_3$): δ7.32 (2H, d, J=8.7 Hz), 6.78 (2H, d, J=8.7 Hz), 6.57 (1H, s, $J_{Sn-H}$=30.9 Hz), 5.20 (2H, br.s), 1.57 (6H, m), 1.34 (6H, m), 1.04 (6H, m), 0.97 (9H, s), 0.91 (9H, t, J=7.2 Hz), 0.19 (6H, s).
$^{13}$C-NMR (ppm, 100 MHz, CDCl$_3$): δ176.1, 155.7, 141.1, 139.3, 129.9, 129.62, 120.0, 28.9, 27.3, 25.6, 18.2, 13.7, 10.4, −4.4

Synthetic Example 8

Synthesis of {(E)-1-tributylstannyl-2-(4-tert-butyldimethylsilyloxyphenyl)}vinyl isocyanate (E)-2-(tributylstannyl)-3-(4-tert-butyldimethylsilyloxyphenyl)acrylamide (1.50 g, 2.65 mmol) prepared in Synthetic Example 7 was dissolved in tetrahydrofuran (27 ml) in nitrogen atmosphere, and lead tetraacetate (1.30 g, 2.91 mmol) was added at room temperature. After stirring for 20 minutes, hexane (27 ml) was added, the solution was subjected to filtration with Celite, and the filtrate was concentrated under reduced pressure. The residue was purified by silica gel column chromatography (hexane:ethyl acetate=50:1) to give {(E)-1-tributylstannyl-2-(4-tert-butyldimethylsilyloxyphenyl)}vinyl isocyanate (1.32 g, 88%) as a colorless oily substance.

IR (film): 2,256 cm$^{-1}$ (—NCO).

$^1$H-NMR (ppm, 300 MHz, CDCl$_3$): δ7.54 (2H, d, J=8.7 Hz), 6.81 (2H, d, J=8.7 Hz), 5.89 (1H, s, $J_{Sn-H}$=16.5 Hz), 1.55 (6H, m), 1.33 (6H, m), 1.08 (6H, m), 0.98 (9H, s), 0.92 (9H, t, J=7.2 Hz), 0.20 (6H, s).
$^{13}$C-NMR (ppm, 75 MHz, CDCl$_3$): δ155.6, 134.0, 131.3, 130.0, 129.4, 125.1, 120.3, 29.3, 27.7, 26.1, 18.7, 14.0, 10.9, −4.0.

Synthetic Example 9

Synthesis of N-{(E)-1-tributylstannyl-2-(4-tert-butyldimethylsilyloxyphenyl)vinyl}formamide {(E)-1-tributylstannyl-2-(4-tert-butyldimethylsilyloxyphenyl)}vinyl isocyanate (26.5 mg, 0.047 mmol) prepared in Synthetic Example 8 was dissolved in tetrahydrofuran (470 ml) in nitrogen atmosphere, and a 1.0 mol/l lithium triethylborohydride/tetrahydrofuran solution (49 ml, 0.049 mmol) was dropwise added at −78° C. After stirring for 30 minutes, a saturated ammonium chloride aqueous solution was added to terminate the reaction, then silica gel was added, the solution was concentrated under reduced pressure to dryness, and the resulting product was purified by silica gel column chromatography (hexane:ethyl acetate=5:1) to give N-{(E)-1-tributylstannyl-2-(4-tert-butyldimethylsilyloxyphenyl)vinyl}formamide (26.1 mg, 98%) as a pale yellow oily substance.

LRFAB-MS (m/z): 568.3, 566.3 [M+H]$^+$; calculated value $C_{27}H_{49}NO_2SiSn$: 567.3, 565.3.
$^1$H-NMR (ppm, 400 MHz, CDCl$_3$): δ8.11 (1H, s), 7.88 (1H, br.s), 7.12 (2H, d, J=8.4 Hz), 6.84 (2H, d, J=8.4 Hz), 5.91 (1H, s, $J_{Sn-H}$=20.4 Hz), 1.53 (6H, m), 1.32 (6H, m), 0.99 (6H, m), 0.98 (9H, s), 0.90 (9H, t, J=7.2 Hz), 0.21 (6H, s).
$^{13}$C-NMR (ppm, 75 MHz, CDCl$_3$): δ159.2, 154.7, 145.8, 135.7, 129.3, 122.8, 120.6, 29.0, 27.3, 25.7, 13.8, 12.1, 8.7, −4.4.

Synthetic Example 10

Synthesis of (E)-2-(tributylstannyl)-3-(3,4-dichlorophenyl)acrylamide 3-(3,4-dichlorophenyl)propionic acid amide (21 mg, 0.1 mmol) prepared in the same manner as in Reference Synthetic Example 8 was dissolved in tetrahydrofuran (2 ml) in nitrogen atmosphere, and under cooling with ice, tetrakistriphenylphosphine palladium(0) (5 mg, 0.004 mmol) was added, and then a tetrahydrofuran solution (0.5 ml) of tri-n-butyltin hydride (35 μl, 0.13 mmol) was dropwise added. After stirring for 30 minutes, the solution was concentrated under reduced pressure, and the residue was purified by tin-layer silica gel column chromatography (hexane:ethyl acetate=3:1) to give (E)-2-(tributylstannyl)-3-(3,4-dichlorophenyl)acrylamide (12.3 mg, 24%) as a pale yellow oily substance.

$^1$H-NMR (ppm, 300 MHz, CDCl$_3$): δ0.7 to 1.8 (27H, m), 5.10 (1H, brs), 5.30 (1H, brs), 6.13 (1H, s), 6.84 (1H, dd, J=8 Hz, J=2 Hz), 7.09 (1H, d, J=2 Hz), 7.45 (1H, d, J=8 Hz)

Synthetic Example 11

Synthesis of (E)-2-(tributylstannyl)-3-(3,4-dimethoxyphenyl)acrylamide 3-(3,4-dimethoxyphenyl)propionic acid amide (20.5 mg, 0.1 mmol) prepared in the same manner as in Reference Synthetic Example 8 was dissolved in tetrahydrofuran (2 ml)

in nitrogen atmosphere, and under cooling with ice, tetrakistriphenylphosphine palladium(0) (5 mg, 0.004 mmol) was added, and then a tetrahydrofuran solution (0.5 ml) of tri-n-butyltin hydride (35 μl, 0.13 mmol) was dropwise added. After stirring for 30 minutes, the solution was concentrated under reduced pressure, and the residue was purified by tin-layer silica gel column chromatography (hexane:ethyl acetate=1:1) to give (E)-2-(tributylstannyl)-3-(3,4-dimethoxyphenyl)acrylamide (14.8 mg, 30%) as a pale yellow oily substance.

$^1$H-NMR (ppm, 300 MHz, CDCl$_3$): δ0.7 to 1.8 (27H, m), 3.88 (6H, s×2), 5.22 (1H, brs), 5.29 (1H, brs), 6.57 (1H, s), 6.70 (1H, s), 6.81 (1H, s), 7.04 (1H, s).

Reference Synthetic Example 9

Synthesis of (1Z,3Z)-2,3-diformamino-bis(4-tert-butyldimethylsilyloxyphenyl)buta-1,3-diene N-{(E)-1-tributylstannyl-2-(4-tert-butyldimethylsilyloxyphenyl)vinyl}formamide (236.6 mg, 0.32 mmol) prepared in Synthetic Example 9 was dissolved in tetrahydrofuran (4.2 ml) in oxygen atmosphere, and copper(I) chloride (92.4 mg, 0.84 mmol) was added under cooling with ice, followed by vigorous stirring for 4 hours. After filtration, silica gel was added to the filtrate, and the filtrate was concentrated under reduced pressure to dryness, and the resulting product was purified by silica gel column chromatography (toluene:acetone=6:1) to give (1Z,3Z)-2,3-diformamino-bis(4-tert-butyldimethylsilyloxyphenyl)buta-1,3-diene (57.8 mg, 50%) as a colorless powder.

Melting point (morphology): 212° C. (decomposed, colorless powder) LRFAB-MS (m/z): 552.2 M$^+$; calculated value C$_{30}$H$_{44}$N$_2$O$_4$Si$_2$: 552.2.

Reference Synthetic Example 10

Synthesis of (1Z, 3Z)-2,3-diisocyano-1,4-bis(4-tert-butyldimethylsilyloxyphenyl)buta-1,3-diene (1Z, 3Z)-2,3-diformamino-bis(4-tert-butyldimethylsilyloxyphenyl)buta-1,3-diene (110.0 mg, 0.20 mmol) prepared in Reference Synthetic Example 9 was dissolved in dichloromethane (1.5 ml) in nitrogen atmosphere, and triethylamine (101 ml, 0.72 mmol) was dropwise added under cooling with ice. Then, triphosgene (59.7 mg, 0.20 mmol) was added, followed by stirring for one hour, and the reaction solution was diluted with ethyl acetate and poured into a saturated sodium hydrogen carbonate aqueous solution. Extraction with ethyl acetate was carried out twice, and the obtained organic layer was concentrated under reduced pressure. The residue was purified by silica gel column chromatography (hexane:ethyl acetate=20:1) to give (1Z, 3Z)-2,3-diisocyano-1,4-bis(4-tert-butyldimethylsilyloxyphenyl)buta-1,3-diene (74.9 mg, 72%) as a yellow powder.

Melting point (morphology): 160° C. (decomposed, yellow powder) LRFAB-MS (m/z): 516.3 M$^+$; calculated value C$_{30}$H$_{40}$N$_2$O$_2$Si$_2$: 516.3.

IR (KBr): 2,117 cm$^{-1}$ (—NC)

$^1$H-NMR (ppm, 400 MHz, CDCl$_3$): δ7.73 (4H, d, J=8.4 Hz), 7.10 (2H, s), 6.92 (4H, d, J=8.8 Hz), 1.00 (18H, s), 0.25 (12H, s).

$^{13}$C-NMR (ppm, 100 MHz, CDCl$_3$): δ173.3, 157.7, 131.7, 127.6, 125.4, 120.6, 116.3, 25.6, 18.2, −4.4.

Reference Synthetic Example 11

Synthesis of (1Z, 3Z)-2,3-diisocyano-1,4-bis(4-hydroxyphenyl)buta-1,3-diene (1Z,3Z)-2,3-diisocyano-1,4-bis(4-tert-butyldimethylsilyloxyphenyl)buta-1,3-diene (74.0 mg, 0.14 mmol) prepared in Reference Synthetic Example 10 was dissolved in tetrahydrofuran in nitrogen atmosphere, and acetic acid (21 ml, 0.36 mmol) was added under cooing with ice. Then, a 1.0 mol/l tetra-n-butylammonium fluoride/tetrahydrofuran solution (280 ml, 0.28 mmol) was slowly added dropwise. The reaction solution was returned to room temperature, followed by stirring for 3 hours, and the reaction solution was purified as it was by silica gel column chromatography (hexane:ethyl acetate=2:1) to give (1Z, 3Z)-2,3-diisocyano-1,4-bis(4-hydroxyphenyl)buta-1,3-diene (48.2 mg, 85%) as a yellow powder.

Melting point (morphology): 135° C. (decomposed, yellow powder) LRFAB-MS (m/z): 289.2 [M+H]$^+$; calculated value C$_{20}$H$_{16}$N$_2$O$_2$: 288.1.

IR (KBr): 2,134 cm$^{-1}$ (—NC).

$^1$H-NMR (ppm, 400 MHz, Acetone-d$_6$): δ7.78 (4H, d, J=8.4 Hz), 7.04 (2H, s), 6.94 (4H, d, J=8.4 Hz).

$^{13}$C-NMR (ppm, 100 MHz, Acetone-d$_6$): δ175.3, 160.8, 133.2, 128.7, 125.2, 117.2, 116.9.

The structural formulae of the compounds obtained in Examples are given below.

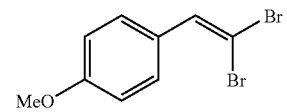

Ref. Syn. Ex. 1

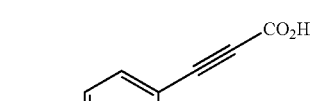

Ref. Syn. Ex. 2

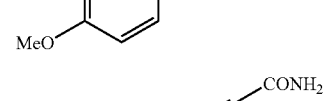

Ref Syn. Ex. 3

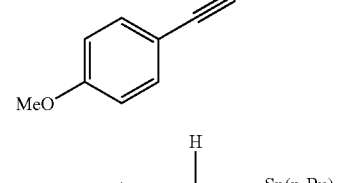

Syn. Ex. 1

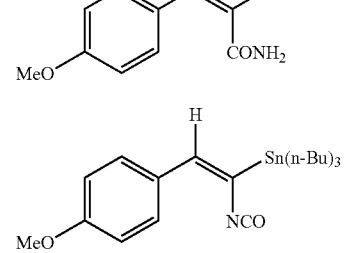

Syn. Ex. 2

Syn. Ex. 3
Syn. Ex. 4
Syn. Ex. 5
Syn. Ex. 6
Syn. Ex. 7
Syn. Ex. 8
Syn. Ex. 9
Syn. Ex. 10
Syn. Ex. 11
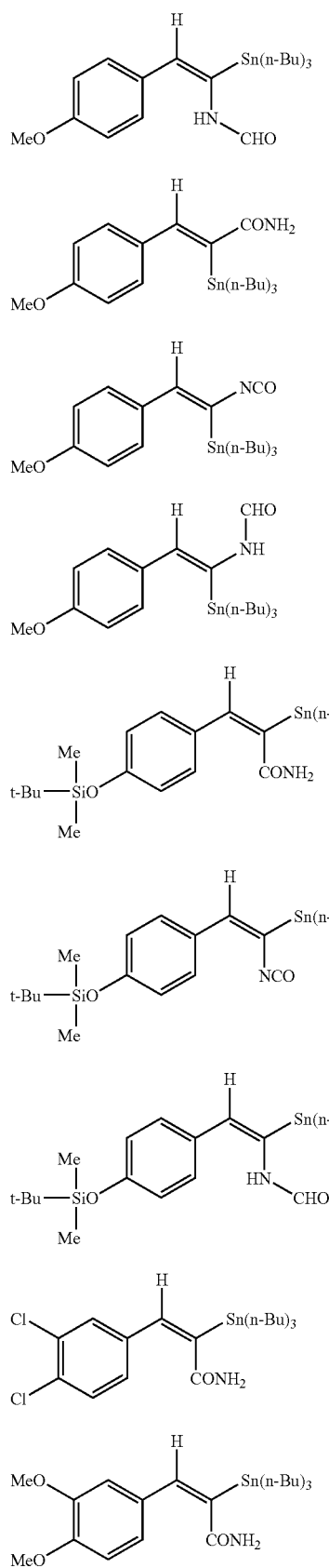
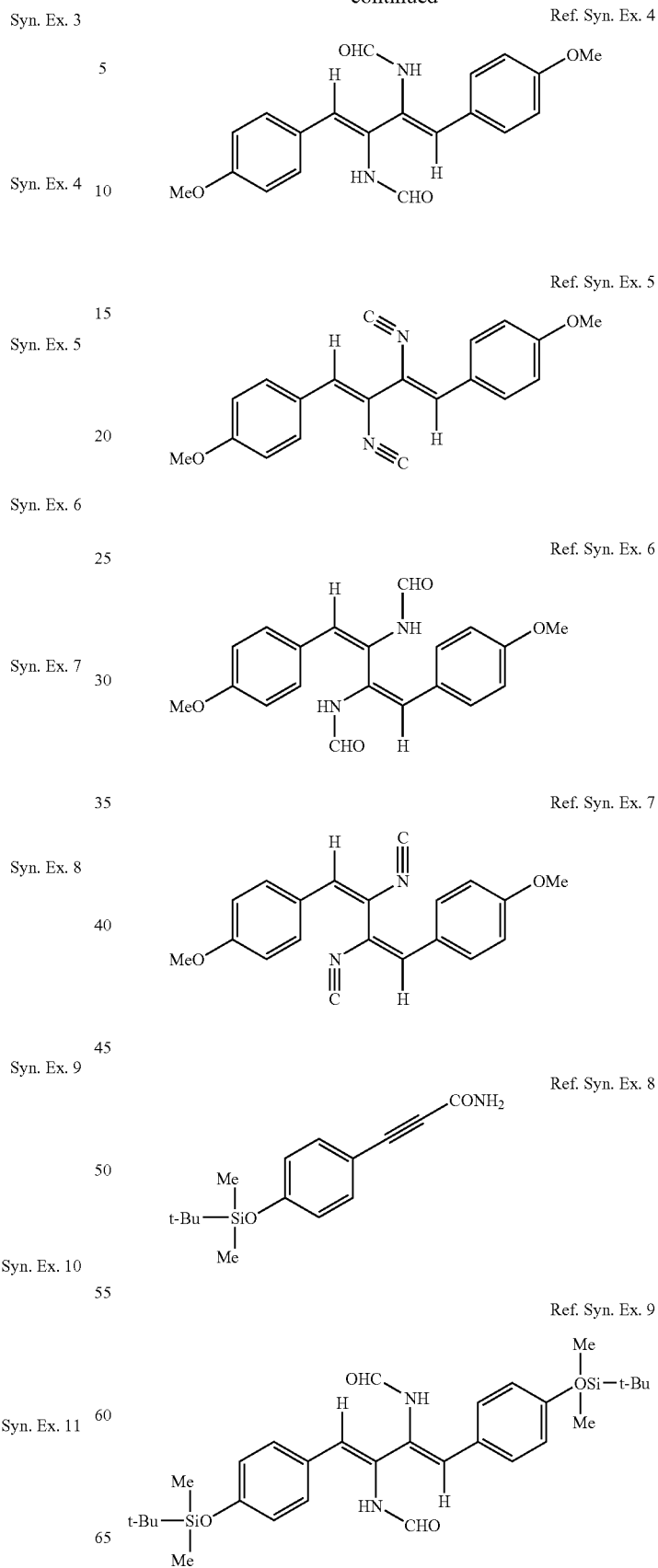
Ref. Syn. Ex. 4
Ref. Syn. Ex. 5
Ref. Syn. Ex. 6
Ref. Syn. Ex. 7
Ref. Syn. Ex. 8
Ref. Syn. Ex. 9

-continued

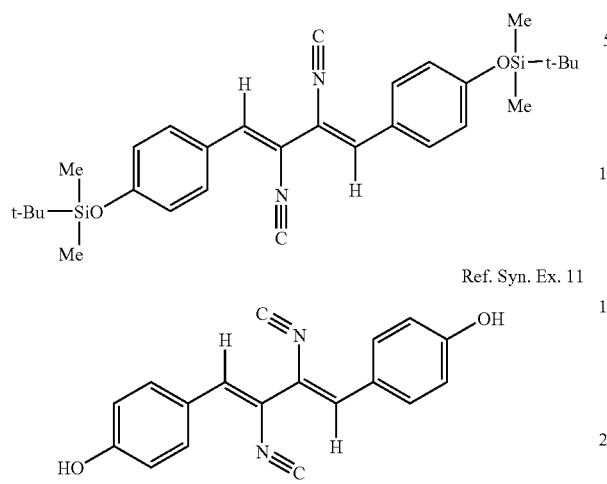

Ref. Syn. Ex. 10

Ref. Syn. Ex. 11

INDUSTRIAL APPLICABILITY

The compounds of the present invention have a tin functional group and at the α-position, functional groups, such as a carbamoyl group, a thiocarbamoyl group, an isocyanate group, an isothiocyanate group, a formylamino group, a thioformylamino group, an isonitrile group, an urea group and a carbamate group, differing in the reactivity, and are thereby capable of being converted to various compounds sequentially by introduction of a substituent and conversion of a functional group depending upon the reactivity and are thereby very useful. Various analogs can be prepared from a common intermediate, and the present invention is particularly useful for creation of function-developing substances such as pharmaceuticals/agrichemicals and functional materials.

The entire disclosures of Japanese Patent Application No. 2005-117593 filed on Apr. 14, 2005 and Japanese Patent Application No. 2005-365795 filed on Dec. 20, 2005 including specifications, claims and summaries are incorporated herein by reference in their entireties.

The invention claimed is:

1. An α-substituted vinyltin compound represented by the formula (1), a tautomer or salt of the compound or a solvate thereof:

wherein $R^1$ is a $C_{1-10}$ alkyl group (the $C_{1-10}$ alkyl group may be substituted by a halogen atom) or a $C_{2-14}$ aryl group (the $C_{2-14}$ group may be substituted by a $C_{1-6}$ alkyl group (the $C_{1-6}$ alkyl group may be substituted by a halogen atom) or a halogen atom);

$R^2$ is a $C_{2-14}$ aryl group, a $C_{2-9}$ heterocyclyl group or a $C_{3-10}$ cycloalkyl group (each of the $C_{2-14}$ aryl group, $C_{2-9}$ heterocyclyl group and $C_{3-10}$ cycloalkyl group may optionally be substituted by a substituent represented by $-W^1(CW^2W^3)mW^4$ (wherein $W^1$ is $(CR^5R^6)n$ (wherein $R^5$ and $R^6$ are each independently a hydrogen atom or a $C_{1-6}$ alkyl group (the $C_{1-6}$ alkyl group may be substituted by a halogen atom) or they together form O= or S=, and n is 0, 1, 2 or 3), an oxygen atom, a sulfur atom or $NR^7$ (wherein $R^7$ is a hydrogen atom, a $C_{1-6}$ alkyl group, a formyl group or a $C_{1-6}$ alkylcarbonyl group), $W^2$ and $W^3$ are each independently a hydrogen atom or a $C_{1-3}$ alkyl group (the $C_{1-3}$ alkyl group may be substituted by a halogen atom), m is 0, 1, 2 or 3, and $W^4$ is a hydrogen atom, a hydroxyl group, a protected hydroxyl group, a thiol group, a protected thiol group, an amino group, a protected amino group, a formyl group, a halogen atom, a nitro group, a cyano group, a $C_{1-10}$ alkyl group, a $C_{1-10}$ thioalkyl group, a $C_{2-10}$ alkenyl group, a $C_{2-6}$ alkynyl group, a $C_{2-9}$ heterocyclyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (each of the $C_{1-10}$ alkyl group, $C_{1-10}$ thioalkyl group, $C_{2-10}$ alkenyl group, $C_{2-6}$ alkynyl group, $C_{2-9}$ heterocyclyl group, $C_{1-10}$ alkoxy group, $C_{1-10}$ alkylcarbonyloxy group, $C_{1-10}$ alkylcarbonylamino group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a thiol group, a protected thiol group, a phosphonic acid group, a phosphonic acid $C_{1-6}$ alkyl ester group, a protected phosphonic acid group, a sulfonic acid group, a sulfonic acid $C_{1-6}$ alkyl ester group, a protected sulfonic acid group, a tetrazole group, a protected tetrazole group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), $S(=O)_2R^8$, $P(=O)_2R^8$, $S(=O)R^8$, $C(=O)R^8$, $C(=S)R^8$ (wherein $R^8$ is a hydroxyl group, a protected hydroxyl group, a $C_{1-10}$ alkyl group, a $C_{2-10}$ alkenyl group, a $C_{2-6}$ alkynyl group, a $C_{2-9}$ heterocyclyl group, a $C_{1-10}$ alkoxy group (each of the $C_{1-10}$ alkyl group, $C_{2-10}$ alkenyl group, $C_{2-6}$ alkynyl group, $C_{2-9}$ heterocyclyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group, a $C_{2-14}$ aryloxy group (each of the $C_{2-14}$ aryl group and $C_{2-14}$ aryloxy group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^9R^{10}$ (wherein $R^9$ and $R^{10}$ are each independently a hydrogen atom, a hydroxyl group, a protected hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^9$ and $R^{10}$ together form $—(CH_2)_{m1}$-G-$(CH_2)_{m2}—$ (wherein G is an oxygen atom, a sulfur atom, $CR^{11}R^{12}$ (wherein $R^{11}$ and $R^{12}$ are each independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{13}$ (wherein $R^{13}$ is a hydrogen atom, a hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m1 and m2 are each independently an integer of from 0 to 5, provided that m1+m2 is 3, 4 or 5))), a tetrazole group or a protected tetrazole group)); and $R^3$ is a carbamoyl group, a thiocarbamoyl group, an isonitrile group, an isocyanate group, an isothiocyanate group, a formylamino group, a thioformylamino group, or $—NH(C=X)R^4$ (wherein X is an oxygen atom or a sulfur atom, $R^4$ is a $C_{1-10}$ thioalkyl group, a $C_{1-10}$ alkoxy group (each of the $C_{1-10}$ thioalkyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^{14}R^{15}$ (wherein $R^{14}$ and $R^{15}$ are each independently a hydrogen atom, a hydroxyl group, a protected hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^{14}$ and $R^{15}$ together form —$(CH_2)_{m3}$-J-$(CH_2)_{m4}$— (wherein J is an oxygen atom, a sulfur atom, $CR^{16}R^{17}$ (wherein $R^{16}$ and $R^{17}$ are each independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{18}$ (wherein $R^{18}$ is a hydrogen atom, a hydroxyl group, a formyl group, a $C_{1-10}$ alkyl group, a $C_{2-10}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-10}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-10}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m3 and m4 are each independently an integer of from 0 to 5, provided that m3+m4 is 3, 4 or 5))).

2. The α-substituted vinyltin compound, a tautomer or salt of the compound or a solvate thereof according to claim 1, which is an E-isomer or a Z-isomer.

3. The α-substituted vinyltin compound, a tautomer or salt of the compound or a solvate thereof according to claim 2, wherein $R^2$ is a $C_{2-14}$ aryl group (the $C_{2-14}$ aryl group may optionally be substituted by a substituent represented by —$W^1(CW^2W^3)mW^4$ (wherein $W^1$ is $(CR^5R^6)n$ (wherein $R^5$ and $R^6$ are each independently a hydrogen atom or a $C_{1-6}$ alkyl group (the $C_{1-6}$ alkyl group may be substituted by a halogen atom) or they together form O= or S=, and n is 0, 1, 2 or 3), an oxygen atom, a sulfur atom or $NR^7$ (wherein $R^7$ is a hydrogen atom, a $C_{1-6}$ alkyl group, a formyl group or a $C_{1-6}$ alkylcarbonyl group), $W^2$ and $W^3$ are each independently a hydrogen atom or a $C_{1-3}$ alkyl group (the $C_{1-3}$ alkyl group may be substituted by a halogen atom), m is 0, 1, 2 or 3, and $W^4$ is a hydrogen atom, a hydroxyl group, a protected hydroxyl group, a thiol group, a protected thiol group, an amino group, a protected amino group, a formyl group, a halogen atom, a nitro group, a cyano group, a $C_{1-10}$ alkyl group, a $C_{1-10}$ thioalkyl group, a $C_{2-6}$ alkenyl group, a $C_{2-6}$ alkynyl group, a $C_{2-9}$ heterocyclyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (each of the $C_{1-10}$ alkyl group, $C_{1-10}$ thioalkyl group, $C_{2-6}$ alkenyl group, $C_{2-6}$ alkynyl group, $C_{2-9}$ heterocyclyl group, $C_{1-10}$ alkoxy group, $C_{1-10}$ alkylcarbonyloxy group, $C_{1-10}$ alkylcarbonylamino group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a thiol group, a protected thiol group, a phosphonic acid group, a phosphonic acid $C_{1-6}$ alkyl ester group, a protected phosphonic acid group, a sulfonic acid group, a sulfonic acid $C_{1-6}$ alkyl ester group, a protected sulfonic acid group, a tetrazole group, a protected tetrazole group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), $S(=O)_2R^8$, $S(=O)R^8$, $P(=O)_2R^8$, $C(=O)R^8$, $C(=S)R^8$ (wherein $R^8$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclyl group, a $C_{1-10}$ alkoxy group (each of the $C_{1-10}$ alkyl group, $C_{2-6}$ alkenyl group, $C_{2-6}$ alkynyl group, $C_{2-9}$ heterocyclyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), a $C_{2-14}$ aryl group, a $C_{2-14}$ aryloxy group (each of the $C_{2-14}$ aryl group and $C_{2-14}$ aryloxy group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^9R^{10}$ (wherein $R^9$ and $R^{10}$ are each independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^9$ and $R^{10}$ together form —$(CH_2)_{m1}$-G-$(CH_2)_{m2}$— (wherein G is an oxygen atom, a sulfur atom, $CR^{11}R^{12}$ (wherein $R^{11}$ and $R^{12}$ are each independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{13}$ (wherein $R^{13}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m1 and m2 are each independently an integer of from 0 to 5, provided that m1+m2 is 3, 4 or 5))), a tetrazole group or a protected tetrazole group)).

4. The α-substituted vinyltin compound, a tautomer or salt of the compound or a solvate thereof according to claim 2, wherein $R^2$ is a phenyl group (the phenyl group may optionally be substituted by a substituent represented by —$W^1$($CW^2W^3$)m$W^4$ (wherein $W^1$ is ($CR^5R^6$)n (wherein $R^5$ and $R^6$ are each independently a hydrogen atom or a $C_{1-6}$ alkyl group (the $C_{1-6}$ alkyl group may be substituted by a halogen atom) or they together form O═ or S═, and n is 0, 1, 2 or 3), an oxygen atom, a sulfur atom or $NR^7$ (wherein $R^7$ is a hydrogen atom, a $C_{1-6}$ alkyl group, a formyl group or a $C_{1-6}$ alkylcarbonyl group), $W^2$ and $W^3$ are each independently a hydrogen atom or a $C_{1-3}$ alkyl group (the $C_{1-3}$ alkyl group may be substituted by a halogen atom), m is 0, 1, 2 or 3, and $W^4$ is a hydrogen atom, a hydroxyl group, a protected hydroxyl group, a thiol group, a protected thiol group, an amino group, a protected amino group, a formyl group, a halogen atom, a nitro group, a cyano group, a $C_{1-10}$ alkyl group, a $C_{1-10}$ thioalkyl group, a $C_{2-6}$ alkenyl group, a $C_{2-6}$ alkynyl group, a $C_{2-9}$ heterocyclyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (each of the $C_{1-10}$ alkyl group, $C_{1-10}$ thioalkyl group, $C_{2-6}$ alkenyl group, $C_{2-6}$ alkynyl group, $C_{2-9}$ heterocyclyl group, $C_{1-10}$ alkoxy group, $C_{1-10}$ alkylcarbonyloxy group, $C_{1-10}$ alkylcarbonylamino group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)), a phenyl group (the phenyl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a thiol group, a protected thiol group, a phosphonic acid group, a phosphonic acid $C_{1-6}$ alkyl ester group, a protected phosphonic acid group, a sulfonic acid group, a sulfonic acid $C_{1-6}$ alkyl ester group, a protected sulfonic acid group, a tetrazole group, a protected tetrazole group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)), S(═O)$_2R^8$, S(═O)$R^8$, P(═O)$_2R^8$, C(═O)$R^8$, C(═S)$R^8$ (wherein $R^8$ is a hydroxyl group, a protected hydroxyl group, a $C_{1-10}$ alkyl group, a $C_{2-6}$ alkenyl group, a $C_{2-6}$ alkynyl group, a $C_{2-9}$ heterocyclyl group, a $C_{1-10}$ alkoxy group (each of the $C_{1-10}$ alkyl group, $C_{2-6}$ alkenyl group, $C_{2-6}$ alkynyl group, $C_{2-9}$ heterocyclyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)), a phenyl group, a phenyloxy group (each of the phenyl group and phenyloxy group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)) or $NR^9R^{10}$ (wherein $R^9$ and $R^{10}$ are each independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)) or a phenyl group (the phenyl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom))), or $R^9$ and $R^{10}$ together form —$(CH_2)_{m1}$-G-$(CH_2)_{m2}$— (wherein G is an oxygen atom, a sulfur atom, $CR^{11}R^{12}$ (wherein $R^{11}$ and $R^{12}$ are each independently a hydrogen atom, a $C_{1-10}$ alkyl group, a phenyl group, a $C_{1-10}$ alkoxy group, a phenyloxy group, a hydroxyl group or a protected hydroxyl group) or $NR^{13}$ (wherein $R^{13}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom)) or a phenyl group (the phenyl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a phenyl group or a phenyloxy group (each of the phenyl group and phenyloxy group may be substituted by a $C_{1-6}$ alkyl group (the $C_{1-6}$ alkyl group may be substituted by a halogen atom) or a halogen atom))), and m1 and m2 are each independently an integer of from 0 to 5, provided that m1+m2 is 3, 4 or 5))), a tetrazole group or a protected tetrazole group)).

5. The α-substituted vinyltin compound, a tautomer or salt of the compound or a solvate thereof according to any one of claims 2 to 4, wherein $R^3$ is a carbamoyl group or a thiocarbamoyl group.

6. The α-substituted vinyltin compound, a tautomer or salt of the compound or a solvate thereof according to any one of claims 2 to 4, wherein $R^3$ is a formylamino group or a thioformylamino group.

7. The α-substituted vinyltin compound, a tautomer or salt of the compound or a solvate thereof according to any one of claims 2 to 4, wherein $R^3$ is an isonitrile group.

8. The α-substituted vinyltin compound, a tautomer or salt of the compound or a solvate thereof according to any one of claims 2 to 4, wherein $R^3$ is an isocyanate group or an isothiocyanate group.

9. The α-substituted vinyltin compound, a tautomer or salt of the compound or a solvate thereof according to any one of claims 2 to 4, wherein $R^3$ is —NH(C=X)$R^4$ (wherein X is an oxygen atom or a sulfur atom, $R^4$ is a $C_{1-10}$ thioalkyl group, a $C_{1-10}$ alkoxy group (each of the $C_{1-10}$ thioalkyl group and $C_{1-10}$ alkoxy group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or $NR^{14}R^{15}$ (wherein $R^{14}$ and $R^{15}$ are each independently a hydrogen atom, a hydroxyl group, a protected hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)), or $R^{14}$ and $R^{15}$ together form —$(CH_2)_{m3}$-J-$(CH_2)_{m4}$— (wherein J is an oxygen atom, a sulfur atom, $CR^{16}R^{17}$ (wherein $R^{16}$ and $R^{17}$ are each independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{18}$ (wherein $R^{18}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylsulfonyl group, a $C_{1-10}$ alkylcarbonyl group (each of the $C_{1-10}$ alkyl group, $C_{2-6}$ alkenyl group, $C_{2-6}$ alkynyl group, $C_{1-10}$ alkoxy group, $C_{1-10}$ alkylcarbonyloxy group, $C_{1-10}$ alkoxycarbonyl group, $C_{1-10}$ alkylsulfonyl group and $C_{1-10}$ alkylcarbonyl group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom)) or a $C_{2-14}$ aryl group (the $C_{2-14}$ aryl group may optionally be substituted by a $C_{1-10}$ alkyl group (the $C_{1-10}$ alkyl group may be substituted by a halogen atom), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))), and m3 and m4 are each independently an integer of from 0 to 5, provided that m3+m4 is 3, 4 or 5))).

10. The α-substituted vinyltin compound, a tautomer or salt of the compound or a solvate thereof according to any one of claims 2 to 4, wherein $R^3$ is —NH(C=X)$R^4$ (wherein X is an oxygen atom or a sulfur atom, and $R^4$ is a $C_{1-10}$ thioalkyl group, a $C_{1-10}$ alkoxy group or a mono- or di-$C_{1-10}$ alkylamino group (each of the $C_{1-10}$ thioalkyl group, $C_{1-10}$ alkoxy group and mono- or di-$C_{1-10}$ alkylamino group may optionally be substituted by a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a protected amino group, a mono- or di-$C_{1-10}$ alkylamino group, a hydroxyl group, a protected hydroxyl group, a $C_{2-14}$ aryl group or a $C_{2-14}$ aryloxy group (each of the $C_{2-14}$ aryl group and $C_{2-14}$ aryloxy group may be substituted by a $C_{1-6}$ alkyl group (the $C_{1-6}$ alkyl group may be substituted by a halogen atom) or a halogen atom))).

11. The α-substituted vinyltin compound, a tautomer or salt of the compound or a solvate thereof according to any one of claims 1 to 4, wherein $R^1$ is a $C_{1-6}$ alkyl group.

12. The α-substituted vinyltin compound, a tautomer or salt of the compound or a solvate thereof according to any one of claims 1 to 4, wherein $R^1$ is a phenyl group.

13. The α-substituted vinyltin compound, a tautomer or salt of the compound or a solvate thereof according to claim 5, wherein $R^1$ is a $C_{1-6}$ alkyl group.

14. The α-substituted vinyltin compound, a tautomer or salt of the compound or a solvate thereof according to claim 6, wherein $R^1$ is a $C_{1-6}$ alkyl group.

15. The α-substituted vinyltin compound, a tautomer or salt of the compound or a solvate thereof according to claim 7, wherein $R^1$ is a $C_{1-6}$ alkyl group.

16. The α-substituted vinyltin compound, a tautomer or salt of the compound or a solvate thereof according to claim 8, wherein $R^1$ is a $C_{1-6}$ alkyl group.

17. The α-substituted vinyltin compound, a tautomer or salt of the compound or a solvate thereof according to claim 9, wherein $R^1$ is a $C_{1-6}$ alkyl group.

18. The α-substituted vinyltin compound, a tautomer or salt of the compound or a solvate thereof according to claim 10, wherein $R^1$ is a $C_{1-6}$ alkyl group.

19. The α-substituted vinyltin compound, a tautomer or salt of the compound or a solvate thereof according to claim 5, wherein $R^1$ is a phenyl group.

20. The α-substituted vinyltin compound, a tautomer or salt of the compound or a solvate thereof according to claim 6, wherein $R^1$ is a phenyl group.

21. The α-substituted vinyltin compound, a tautomer or salt of the compound or a solvate thereof according to claim 7, wherein $R^1$ is a phenyl group.

22. The α-substituted vinyltin compound, a tautomer or salt of the compound or a solvate thereof according to claim 8, wherein $R^1$ is a phenyl group.

23. The α-substituted vinyltin compound, a tautomer or salt of the compound or a solvate thereof according to claim 9, wherein $R^1$ is a phenyl group.

24. The α-substituted vinyltin compound, a tautomer or salt of the compound or a solvate thereof according to claim 10, wherein $R^1$ is a phenyl group.

* * * * *